(12) United States Patent
Fischell et al.

(10) Patent No.: US 9,468,383 B2
(45) Date of Patent: Oct. 18, 2016

(54) SYSTEM FOR DETECTING CARDIAC ISCHEMIA AND IRREGULAR HEART RHYTHMS

(71) Applicant: ANGEL MEDICAL SYSTEMS, INC., Fair Haven, NJ (US)

(72) Inventors: David R. Fischell, Fair Haven, NJ (US); Tim A. Fischell, Kalamazoo, MI (US); Jonathan Harwood, Rumson, NJ (US); Robert E. Fischell, Dayton, MD (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

(21) Appl. No.: 14/749,873

(22) Filed: Jun. 25, 2015

(65) Prior Publication Data

US 2015/0289774 A1   Oct. 15, 2015

Related U.S. Application Data

(60) Continuation of application No. 13/025,476, filed on Feb. 11, 2011, now Pat. No. 9,101,278, which is a division of application No. 11/930,027, filed on Oct. 30, 2007, now abandoned, which is a continuation of application No. 10/642,245, filed on Aug. 18, 2003, now Pat. No. 8,030,624, which is a continuation-in-part of application No. 10/251,505, filed on Sep. 20, 2002, now Pat. No. 6,609,023.

(51) Int. Cl.
*A61B 5/0452* (2006.01)
*A61B 5/0245* (2006.01)
*A61B 5/0468* (2006.01)
*A61B 5/00* (2006.01)
*A61B 5/04* (2006.01)
*A61B 5/042* (2006.01)
*A61B 5/0456* (2006.01)
*A61B 5/0472* (2006.01)

(52) U.S. Cl.
CPC ......... *A61B 5/02455* (2013.01); *A61B 5/0031* (2013.01); *A61B 5/04012* (2013.01); *A61B 5/0422* (2013.01); *A61B 5/0452* (2013.01); *A61B 5/0456* (2013.01); *A61B 5/0468* (2013.01); *A61B 5/0472* (2013.01); *A61B 5/746* (2013.01); *A61B 2560/0209* (2013.01)

(58) Field of Classification Search
CPC ........... A61B 5/02455; A61B 5/0468; A61B 5/04012; A61B 5/0464
See application file for complete search history.

(56) References Cited

U.S. PATENT DOCUMENTS 6,609,023 B1 * 8/2003 Fischell et al. ............... 600/515

* cited by examiner

*Primary Examiner* — George Evanisko
(74) *Attorney, Agent, or Firm* — Rosenberg, Klein & Lee

(57) ABSTRACT

A system for detecting acute ischemia includes at least two sensors configured for obtaining electrical signals from a patient's heart, analog-to-digital converter circuitry for digitizing the signal to produce data segments, and a processor configured to analyze data segments to determine if they represent an abnormal heart rhythm. Certain types of abnormal rhythm segments are also checked for acute ischemia. If enough of the abnormal heart rhythm segments manifest acute ischemia, a first type of alarm event is generated. If persistent abnormal heart rhythm segments do not manifest acute ischemia, a second type of alarm event is generated.

7 Claims, 15 Drawing Sheets

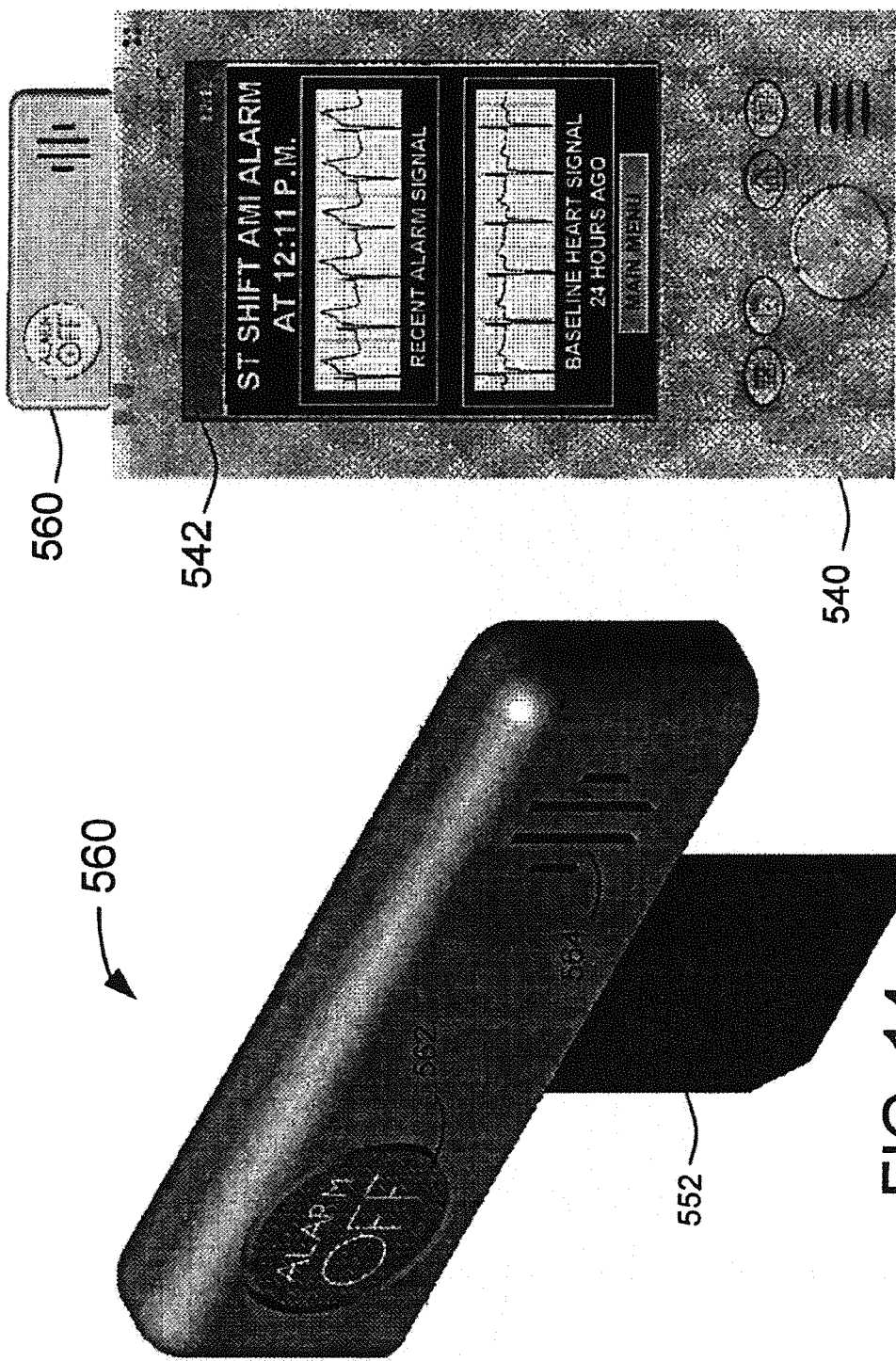

SYSTEM FOR DETECTING CARDIAC ISCHEMIA AND IRREGULAR HEART RHYTHMS

CROSS REFERENCE TO RELATED APPLICATIONS

This application is being filed as a Continuation of application Ser. No. 13/025,476, filed 11 Feb. 2011, currently pending, entitled "RR Interval Based Beat Rejection for a Cardiac Monitor", which is a divisional of U.S. application Ser. No. 11/930,027, filed 30 Oct. 2007, now abandoned, entitled "Cardiac Event Detection System with Adaptive Heart Signal Parameter Analysis" which is a continuation of U.S. application Ser. No. 10/642,245, filed Aug. 18, 2003, now U.S. Pat. No. 8,030,624, issued on 18 Oct. 2011, entitled "System for the Detection of Cardiac Events," which is a Continuation-In-Part of U.S. patent application Ser. No. 10/251,505, filed Sep. 20, 2002, now U.S. Pat. No. 6,609,023 entitled "System for the Detection of Cardiac Events", all of the Related Applications and Patents being hereby Incorporated by Reference.

FIELD OF USE

This invention is in the field of systems, including devices implanted within a human patient, for the purpose of automatically detecting the onset of a cardiac event.

BACKGROUND OF THE INVENTION

Heart disease is the leading cause of death in the United States. A heart attack (also known as an Acute Myocardial Infarction (AMI)) typically results from a thrombus that obstructs blood flow in one or more coronary arteries. AMI is a common and life-threatening complication of coronary heart disease. The sooner that perfusion of the myocardium is restored (e.g., with injection of a thrombolytic medication such as tissue plasminogen activator (tPA)), the better the prognosis and survival of the patient from the heart attack. The extent of damage to the myocardium is strongly dependent upon the length of time prior to restoration of blood flow to the heart muscle.

Myocardial ischemia is caused by a temporary imbalance of blood (oxygen) supply and demand in the heart muscle. It is typically provoked by physical activity or other causes of increased heart rate when one or more of the coronary arteries are obstructed by atherosclerosis. Patients will often (but not always) experience chest discomfort (angina) when the heart muscle is experiencing ischemia.

Acute myocardial infarction and ischemia may be detected from a patient's electrocardiogram (ECG) by noting an ST segment shift (i.e., voltage change) over a relatively short (less than 5 minutes) period of time. However, without knowing the patient's normal ECG pattern detection from standard 12 lead ECG can be unreliable. In addition, ideal placement of subcutaneous electrodes for detection of ST segment shifts as they would relate to a subcutaneously implanted device has not been explored in the prior art.

Fischell et al in U.S. Pat. Nos. 6,112,116 and 6,272,379 describe implantable systems for detecting the onset of acute myocardial infarction and providing both treatment and alarming to the patient. While Fischell et al discuss the detection of a shift in the S-T segment of the patient's electrogram from an electrode within the heart as the trigger for alarms; it may be desirable to provide more sophisticated detection algorithms to reduce the probability of false positive and false negative detection. In addition while these patents describe some desirable aspects of programming such systems, it may be desirable to provide additional programmability and alarm control features.

Although anti-tachycardia pacemakers and Implantable Cardiac Defibrillators (ICDs) can detect heart arrhythmias, none are currently designed to detect ischemia and acute myocardial infarction events independently or in conjunction with arrhythmias.

In U.S. Pat. Nos. 6,112,116 and 6,272,379 Fischell et al, discuss the storage of recorded electrogram and/or electrocardiogram data; however techniques to optimally store the appropriate electrogram and/or electrocardiogram data and other appropriate data in a limited amount of system memory are not detailed.

In U.S. Pat. No. 5,497,780 by M. Zehender, a device is described that has a "goal of eliminating . . . cardiac rhythm abnormality." To do this, Zehender requires exactly two electrodes placed within the heart and exactly one electrode placed outside the heart. Although multiple electrodes could be used, the most practical sensor for providing an electrogram to detect a heart attack would use a single electrode placed within or near to the heart.

Zehender's drawing of the algorithm consists of a single box labeled ST SIGNAL ANALYSIS with no details of what the analysis comprises. His only description of his detection algorithm is to use a comparison of the ECG to a reference signal of a normal ECG curve. Zehender does not discuss any details to teach an algorithm by which such a comparison can be made, nor does Zehender explain how one identifies the "normal ECG curve". Each patient will likely have a different "normal" baseline ECG that will be an essential part of any system or algorithm for detection of a heart attack or ischemia.

In addition, Zehender suggests that an ST signal analysis should be carried out every three minutes. It may be desirable to use both longer and shorter time intervals than 3 minutes so as to capture certain changes in ECG that are seen early on or later on in the evolution of an acute myocardial infarction. Longer observation periods will also be important to account for minor slowly evolving changes in the "baseline" ECG. Zehender has no mention of detection of ischemia having different normal curves based on heart rate. To differentiate from exercise induced ischemia and acute myocardial infarction, it may be important to correlate ST segment shifts with heart rate or R-R interval.

Finally, Zehender teaches that "if an insufficient blood supply in comparison to the reference signal occurs, the corresponding abnormal ST segments can be stored in the memory in digital form or as a numerical event in order to be available for associated telemetry at any time." Storing only abnormal ECG segments may miss important changes in baseline ECG. Thus it is desirable to store some historical ECG segments in memory even if they are not "abnormal".

The Reveal™ subcutaneous loop Holter monitor sold by Medtronic uses two case electrodes spaced by about 3 inches to record electrocardiogram information looking for arrhythmias. It has no real capability to detect ST segment shift and its high pass filtering would in fact preclude accurate detection of changes in the low frequency aspects of the heart's electrical signal. Also the spacing of the electrodes it too close together to be able to effectively detect and record ST segment shifts. Similarly, current external Holter monitors are primarily designed for capturing arrhythmia related signals from the heart.

Although often described as an electrocardiogram (ECG), the stored electrical signal from the heart as measured from electrodes within the body should be termed an "electrogram". The early detection of an acute myocardial infarction or exercise induced myocardial ischemia caused by an increased heart rate or exertion is feasible using a system that notes a change in a patient's electrogram. The portion of such a system that includes the means to detect a cardiac event is defined herein as a "cardiosaver" and the entire system including the cardiosaver and the external portions of the system is defined herein as a "guardian system."

Furthermore, although the masculine pronouns "he" and "his" are used herein, it should be understood that the patient or the medical practitioner who treats the patient could be a man or a woman. Still further the term; "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst. A "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, and premature ventricular or atrial contractions (PVCs or PACs).

For the purposes of this specification, the terms "detection" and "identification" of a cardiac event have the same meaning.

For the purpose of this invention, the term "electrocardiogram" is defined to be the heart electrical signals from one or more skin surface electrode(s) that are placed in a position to indicate the heart's electrical activity (depolarization and repolarization). An electrocardiogram segment refers to the recording of electrocardiogram data for either a specific length of time, such as 10 seconds, or a specific number of heart beats, such as 10 beats. For the purposes of this specification the PQ segment of a patient's electrocardiogram is the typically flat segment of a beat of an electrocardiogram that occurs just before the R wave.

For the purpose of this invention, the term "electrogram" is defined to be the heart electrical signals from one or more implanted electrode(s) that are placed in a position to indicate the heart's electrical activity (depolarization and repolarization). An electrogram segment refers to the recording of electrogram data for either a specific length of time, such as 10 seconds, or a specific number of heart beats, such as 10 beats. For the purposes of this specification the PQ segment of a patient's electrogram is the typically flat segment of an electrogram that occurs just before the R wave. For the purposes of this specification, the terms "detection" and "identification" of a cardiac event have the same meaning. A beat is defined as a sub-segment of an electrogram or electrocardiogram segment containing exactly one R wave.

Heart signal parameters are defined to be any measured or calculated value created during the processing of one or more beats of electrogram data. Heart signal parameters include PQ segment average value, ST segment average value, R wave peak value, ST deviation, ST shift, average signal strength, T wave peak height, T wave average value, T wave deviation, heart rate and R-R interval.

SUMMARY OF THE INVENTION

The present invention is a system for the detection of cardiac events (a guardian system) that includes a device called a cardiosaver, a physician's programmer and an external alarm system. The present invention envisions a system for early detection of an acute myocardial infarction or exercise induced myocardial ischemia caused by an increased heart rate or exertion.

In the preferred embodiment of the present invention, the cardiosaver is implanted along with the electrodes. In an alternate embodiment, the cardiosaver and the electrodes could be external but attached to the patient's body. Although the following descriptions of the present invention in most cases refer to the preferred embodiment of an implanted cardiosaver processing electrogram data from implanted electrodes, the techniques described are equally applicable to the alternate embodiment where the external cardiosaver processes electrocardiogram data from skin surface electrodes.

In the preferred embodiment of the cardiosaver either or both subcutaneous electrodes or electrodes located on a pacemaker type right ventricular or atrial leads will be used. It is also envisioned that one or more electrodes may be placed within the superior vena cava. One version of the implanted cardiosaver device using subcutaneous electrodes would have an electrode located under the skin on the patient's left side. This could be best located between 2 and 20 inches below the patient's left arm pit. The cardiosaver case that would act as the indifferent electrode would typically be implanted like a pacemaker under the skin on the left side of the patient's chest.

Using one or more detection algorithms, the cardiosaver can detect a change in the patient's electrogram that is indicative of a cardiac event, such as an acute myocardial infarction, within five minutes after it occurs and then automatically warn the patient that the event is occurring. To provide this warning, the guardian system includes an internal alarm sub-system (internal alarm means) within the cardiosaver and/or an external alarm system (external alarm means). In the preferred, implanted embodiment, the cardiosaver communicates with the external alarm system using a wireless radio-frequency (RF) signal.

The internal alarm means generates an internal alarm signal to warn the patient. The internal alarm signal may be a mechanical vibration, a sound or a subcutaneous electrical tickle. The external alarm system (external alarm means) will generate an external alarm signal to warn the patient. The external alarm signal is typically a sound that can be used alone or in combination with the internal alarm signal. The internal or external alarm signals would be used to alert the patient to at least two different types of conditions: a major event alarm signaling the detection of a major cardiac event (e.g. a heart attack) and the need for immediate medical attention, and a less critical "SEE DOCTOR" alarm signaling the detection of a less serious non life threatening condition such as exercise induced ischemia. The SEE DOCTOR alarm signal would be used to tell the patient that he is not in immediate danger but should arrange an appointment with his doctor in the near future. In addition to the signaling of less critical cardiac events, the SEE DOCTOR alarm signal could also signal the patient when the cardiosaver battery is getting low.

In the preferred embodiment, in a major event alarm the internal alarm signal would be applied periodically, for example, with three pulses every 5 seconds after the detection of a major cardiac event. It is also envisioned that the less critical "SEE DOCTOR" alarm, would be signaled in a different way, such as one pulse every 7 seconds.

The external alarm system is a hand-held portable device that may include any or all the following features:

1. an external alarm means to generate an external alarm signal to alert the patient.
2. the capability to receive cardiac event alarm, recorded electrogram and other data from the cardiosaver
3. the capability to transmit the cardiac event alarm, recorded electrogram and other data collected by the cardiosaver to a medical practitioner at a remote location.
4. an "alarm-off" button that when depressed can acknowledge that the patient is aware of the alarm and will turn off internal and external alarm signals.
5. a display (typically an LCD panel) to provide information and/or instructions to the patient by a text message and the display of segments of the patient's electrogram.
6. the ability to provide messages including instructions to the patient via a pre-recorded human voice.
7. a patient initiated electrogram capture initiated by a "Panic Button" to allow the patient, even when there has been no alarm, to initiate transmission of electrogram data from the cardiosaver to the external alarm system for transmission to a medical practitioner.
8. a patient initiated electrogram capture to initiate transmission of electrogram data from the cardiosaver to the external alarm system for display to a medical practitioner using the display on the external alarm system.
9. the capability to automatically turn the internal and external alarms off after a reasonable time period that is typically less than 30 minutes if the alarm-off button is not used.

Text and/or spoken instructions may include a message that the patient should promptly take some predetermined medication such as chewing an aspirin, placing a nitroglycerine tablet under his tongue, inhaling or nasal spraying a single or multiple drug combination and/or injecting thrombolytic drugs into a subcutaneous drug port. The messaging displayed by or spoken from the external alarm system and/or a phone call from a medical practitioner who receives the alarm could also inform the patient that he should wait for the arrival of emergency medical services or he should promptly proceed to an emergency medical facility. It is envisioned that the external alarm system can have direct connection to a telephone line and/or work through cell phone or other wireless networks.

If a patient seeks care in an emergency room, the external alarm system could provide a display to the medical practitioners in the emergency room of both the electrogram segment that caused the alarm and the baseline electrogram segment against which the electrogram that caused the alarm was compared. The ability to display both baseline and alarm electrogram segments will significantly improve the ability of the emergency room physician to properly identify AMI.

The preferred embodiment of the external alarm system consists of an external alarm transceiver and a handheld computer. The external alarm transceiver having a standardized interface, such as Compact Flash adapter interface, a secure digital (SD) card interface, a multi-media card interface, a memory stick interface or a PCMCIA card interface. The standardized interface will allow the external alarm transceiver to connect into a similar standardized interface slot that is present in many handheld computers such as a Palm Pilot or Pocket PC. An advantage of this embodiment is that the handheld computer can cost effectively supply the capability for text and graphics display and for playing spoken messages.

Using a handheld computer, such as the Thera™ and by Audiovox™ that combines a Pocket PC with having an SD/Multimedia interface slot with a cell phone having wireless internet access, is a solution that can easily be programmed to provide communication between the external alarm system and a diagnostic center staffed with medical practitioners.

The panic button feature, which allows a patient-initiated electrogram capture and transmission to a medical practitioner, will provide the patient with a sense of security knowing that, if he detects symptoms of a heart-related ailment such as left arm pain, chest pain or palpitations, he can get a fast review of his electrogram. Such a review would allow the diagnosis of arrhythmias, such as premature atrial or ventricular beats, atrial fibrillation, atrial flutter or other heart rhythm irregularities. The medical practitioner could then advise the patient what action, if any, should be taken. The guardian system would also be programmed to send an alarm in the case of ventricular fibrillation so that a caretaker of the patient could be informed to immediately provide a defibrillation electrical stimulus. This is practical as home defibrillation units are now commercially available. It is also possible that, in patients prone to ventricular fibrillation following a myocardial infarction, such a home defibrillator could be placed on the patient's chest to allow rapid defibrillation should ventricular fibrillation occur while waiting for the emergency medical services to arrive.

The physician's programmer provides the patient's doctor with the capability to set cardiosaver cardiac event detection parameters. The programmer communicates with the cardiosaver using the wireless communication capability that also allows the external alarm system to communicate with the cardiosaver. The programmer can also be used to upload and review electrogram data captured by the cardiosaver including electrogram segments captured before, during and after a cardiac event.

An extremely important capability of the present invention is the use of a continuously adapting cardiac event detection program that compares extracted features from a recently captured electrogram segment with the same features extracted from a baseline electrogram segment at a predetermined time in the past. For example, the thresholds for detecting an excessive ST shift would be appropriately adjusted to account for slow changes in electrode sensitivity or ST segment levels over time. It may also be desirable to choose the predetermined time in the past for comparison to take into account daily cycles in the patient's heart electrical signals. Thus, a preferred embodiment of the present invention would use a baseline for comparison that is collected approximately 24 hours prior to the electrogram segment being examined. Such a system would adapt to both minor (benign) slow changes in the patient's baseline electrogram as well as any daily cycle.

Use of a system that adapts to slowly changing baseline conditions is of great importance in the time following the implantation of electrode leads in the heart. This is because there can be a significant "injury current" present just after implantation of an electrode and for a time of up to a month, as the implanted electrode heals into the wall of the heart. Such an injury current may produce a depressed ST segment that deviates from a normal isoelectric electrogram where the PQ and ST segments are at approximately the same voltage. Although the ST segment may be depressed due to this injury current, the occurrence of an acute myocardial infarction can still be detected since an acute myocardial infarction will still cause a significant shift from this "injury current" ST baseline electrogram. Alternately, the present invention might be implanted and the detector could be turned on after healing of the electrodes into the wall of the heart. This healing would be noted in most cases by the evolution to an isoelectric electrogram (i.e., PQ and ST segments with approximately the same voltages).

The present invention's ST detection technique involves recording and processing baseline electrogram segments to calculate the threshold for myocardial infarction and/or ischemia detection. These baseline electrogram segments would typically be collected, processed and stored once an hour or with any other appropriate time interval.

A preferred embodiment of the present invention would save and process a 10 second baseline electrogram segment once every hour. Every 30 seconds the cardiosaver would save and process a 10 second long recent electrogram segment. The cardiosaver would compare the recent electrogram segment with the baseline electrogram segment from approximately 24 hours before (i.e. 24±½ hour before).

The processing of each of the hourly baseline electrogram segments would involve calculating the average electrogram signal strength as well as calculating the average "ST deviation". The ST deviation for a single beat of an electrogram segment is defined to be the difference between the average ST segment voltage and the average PQ segment voltage. The average ST deviation of the baseline electrogram segment is the average of the ST deviation of multiple (at least two) beats within the baseline electrogram segment.

The following detailed description of the drawings fully describes how the ST and PQ segments are measured and averaged.

An important aspect of the present invention is the capability to adjust the location in time and duration of the ST and PQ segments used for the calculation of ST shifts. The present invention is initially programmed with the time interval between peak of the R wave of a beat and the start of the PQ and ST segments of that beat set for the patient's normal heart rate. As the patient's heart rate changes during daily activities, the present invention will adjust these time intervals for each beat proportional to the R-R interval for that beat. In other words, if the R-R interval shortens (higher heart rate) then the ST and PQ segments would move closer to the R wave peak and would become shorter. ST and PQ segments of a beat within an electrogram segment are defined herein as sub-segments of the electrogram segment. Specifically, the time interval between the R wave and the start of the ST and PQ segments may be adjusted in proportion to the R-R interval or alternately by the square root of the R-R interval. It is preferable in all cases to base these times on the R-R interval from the beat before the current beat. As calculating the square root is a processor intensive calculation, the preferred implementation of this feature is best done by pre-calculating the values for the start of PQ and ST segments during programming and loading these times into a simple lookup table where for each R-R interval, the start times and/or durations for the segments is stored.

The difference between the ST deviation on any single beat in a recently collected electrogram segment and a baseline average ST deviation extracted from a baseline electrogram segment is defined herein as the "ST shift" for that beat. The present invention envisions that detection of acute myocardial infarction and/or ischemia would be based on comparing the ST shift of one or more beats with a predetermined detection threshold "$H_{ST}$".

In U.S. application Ser. No. 10/051,743 that is incorporated herein by reference, Fischell describes a fixed threshold for detection that is programmed by the patient's doctor. The present invention envisions that the threshold should rather be based on some percentage "$P_{ST}$" of the average signal strength extracted from the baseline electrogram segment where $P_{ST}$ is a programmable parameter of the cardiosaver device. The "signal strength" can be measured as peak signal voltage, RMS signal voltage or as some other indication of signal strength such as the difference between the average PQ segment amplitude and the peak R wave amplitude.

Similarly, it is envisioned that the value of $P_{ST}$ might be adjusted as a function of heart rate so that a higher threshold could be used if the heart rate is elevated, so as to not trigger on exercise that in some patients will cause minor ST segment shifts when there is not a heart attack occurring. Alternately, lower thresholds might be used with higher heart rates to enhance sensitivity to detect exercise-induced ischemia. One embodiment of the present invention has a table stored in memory where values of $P_{ST}$ for a preset number of heart rate ranges, (e.g. 50-80, 81-90, 91-100, 101-120, 121-140) might be stored for use by the cardiosaver detection algorithm in determining if an acute myocardial infarction or exercise induced ischemia is present.

Thus it is envisioned that the present invention would use the baseline electrogram segments in 3 ways.
1. To calculate a baseline average value of a feature such as ST deviation that is then subtracted from the value of the same feature in recently captured electrogram segments to calculate the shift in the value of that feature. E.g. the baseline average ST deviation is subtracted from the amplitude of the ST deviation on each beat in a recently captured electrogram segment to yield the ST shift for that beat.
2. To provide an average signal strength used in calculating the threshold for detection of a cardiac event. This will improve detection by compensating for slow changes in electrogram signal strength over relatively long periods of time.
3. To provide a medical practitioner with information that will facilitate diagnosis of the patient's condition. For example, the baseline electrogram segment may be transmitted to a remotely located medical practitioner and/or displayed directly to a medical practitioner in the emergency room.

For the purposes of the present invention, the term adaptive detection algorithm is hereby defined as a detection algorithm for a cardiac event where at least one detection-related threshold adapts over time so as to compensate for relatively slow (longer than an hour) changes in the patient's normal electrogram.

It is also envisioned that the present invention could have specific programming to identify a very low heart rate (bradycardia) or a very high heart rate (tachycardia or fibrillation). While a very low heart rate is usually not of immediate danger to the patient, its persistence could indicate the need for a pacemaker. As a result, the present invention could use the "SEE DOCTOR" alarm along with an optional message sent to the external alarm system to alert the patient that his heart rate is too low and that he should see his doctor as soon as convenient. On the other hand, a very high heart rate can signal immediate danger thus it would be desirable to alarm the patient in a manner similar to that of acute myocardial infarction detection. What is more, detections of excessive ST shift during high heart rates may be difficult and if the high heart rate is the result of a heart attack then it is envisioned that the programming of the present invention would use a major event counter that would turn on the alarm if the device detects a combination of excessive ST shift and overly high heart rate.

Another early indication of acute myocardial infarction is a rapid change in the morphology of the T wave. Unfortunately, there are many non-AMI causes of changes in the morphology of a T wave. However, these changes typically occur slowly while the changes from an AMI occur rapidly. Therefore one embodiment of this invention uses detection of a change in the T wave as compared to a baseline collected a short time (less than 30 minutes) in the past. The best embodiment is probably using a baseline collected between 1 and 5 minutes in the past. Such a T wave detector could look at the amplitude of the peak of the T wave. An alternate embodiment of the T wave detector might look at the average value of the entire T wave as compared to the baseline. The threshold for T wave shift detection, like that of ST shift detection, can be a percentage $P_T$ of the average signal strength of the baseline electrogram segment. $P_T$ could differ from $P_{ST}$ if both detectors are used simultaneously by the cardiosaver.

In its simplest form, the "guardian system" includes only the cardiosaver and a physician's programmer. Although the cardiosaver could function without an external alarm system where the internal alarm signal stays on for a preset period of time, the external alarm system is highly desirable. One reason it is desirable is the button on the external alarm system that provides the means for of turning off the alarm in either or both the implanted device (cardiosaver) and the external alarm system. Another very important function of the external alarm system is to facilitate display of both the baseline and alarm electrogram segments to a treating physician to facilitate rapid diagnosis and treatment for the patient.

Thus it is an object of this invention is to have a cardiosaver designed to detect the occurrence of a cardiac event by comparing baseline electrogram data from a first predetermined time with recent electrogram data from a second predetermined time.

Another object of the present invention is to have a cardiac event detected by comparing at least one heart signal parameter extracted from an electrogram segment captured at a first predetermined time by an implantable cardiosaver with the same at least one heart signal parameter extracted from an electrogram segment captured at a second predetermined time.

Another object of the present invention is to have acute myocardial infarction detected by comparing recent electrogram data to baseline electrogram data from the same time of day (i.e. approximately 24 hours in the past).

Another object of the present invention is to have acute myocardial infarction detected by comparing the ST deviation of the beats in a recently collected electrogram segment to the average ST deviation of two or more beats of a baseline electrogram segment.

Another object of the present invention is to have the threshold(s) for detecting the occurrence of a cardiac event adjusted by a cardiosaver device to compensate for slow changes in the average signal level of the patient's electrogram.

Another object of the present invention is to have the threshold for detection of a cardiac event adjusted by a cardiosaver device to compensate for daily cyclic changes in the average signal level of the patient's electrogram.

Another object of the present invention is to have an external alarm system including an alarm off button that will turn off either or both internal and external alarm signals initiated by an implanted cardiosaver.

Another object of the present invention is to have the alarm signal generated by a cardiosaver automatically turn off after a preset period of time.

Still another object of this invention is to use the cardiosaver to warn the patient that an acute myocardial infarction has occurred by means of a subcutaneous vibration.

Still another object of this invention is to have the cardiac event detection require that at least a majority of the beats exhibit an excessive ST shift before identifying an acute myocardial infarction.

Still another object of this invention is to have the cardiac event detection require that excessive ST shift still be present in at least two electrogram segments separated by a preset period of time.

Still another object of this invention is to have the cardiac event detection require that excessive ST shift still be present in at least three electrogram segments separated by preset periods of time.

Yet another object of the present invention is to have a threshold for detection of excessive ST shift that is dependent upon the average signal strength calculated from a baseline electrogram segment.

Yet another object of the present invention is to have a threshold for detection of excessive ST shift that is a function of the difference between the average PQ segment amplitude and the R wave peak amplitude of a baseline electrogram segment.

Yet another object of the present invention is to have a threshold for detection of excessive ST shift that is a function of the average minimum to maximum amplitude for at least two beats calculated from a baseline electrogram segment.

Yet another object of the present invention is to have the ability to detect a cardiac event by the shift in the amplitude of the T wave of an electrogram segment at a second predetermined time as compared with the average baseline T wave amplitude from a baseline electrogram segment at a first predetermined time.

Yet another object of the present invention is to have the ability to detect a cardiac event by the shift in the T wave deviation of at least one beat of an electrogram segment at a second predetermined time as compared with the average baseline T wave deviation from an electrogram segment at a first predetermined time.

Yet another object of the present invention is to have the first and second predetermined times for T wave amplitude and/or deviation comparison be separated by less than 30 minutes.

Yet another object of the present invention is to have the baseline electrogram segment used for ST segment shift detection and the baseline electrogram segment used for T wave shift detection be collected at different times.

Yet another object of the present invention is to have an individualized (patient specific) "normal" heart rate range such that the upper and lower limits of "normal" are programmable using the cardiosaver programmer.

Yet another object of the present invention is to have one or more individualized (patient specific) "elevated" heart rate ranges such that the upper and lower limits of each "elevated" range are programmable using the cardiosaver programmer.

Yet another object of the present invention is to allow the threshold for detection of an excessive ST shift be different for the "normal" heart rate range as compared to one or more "elevated" heart rate ranges.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 14 illustrates the preferred physical embodiment of the external alarm transceiver.

FIG. 15 illustrates the physical embodiment of the combined external alarm transceiver and pocket PC.

DETAILED DESCRIPTION OF THE INVENTION

Figure 1:
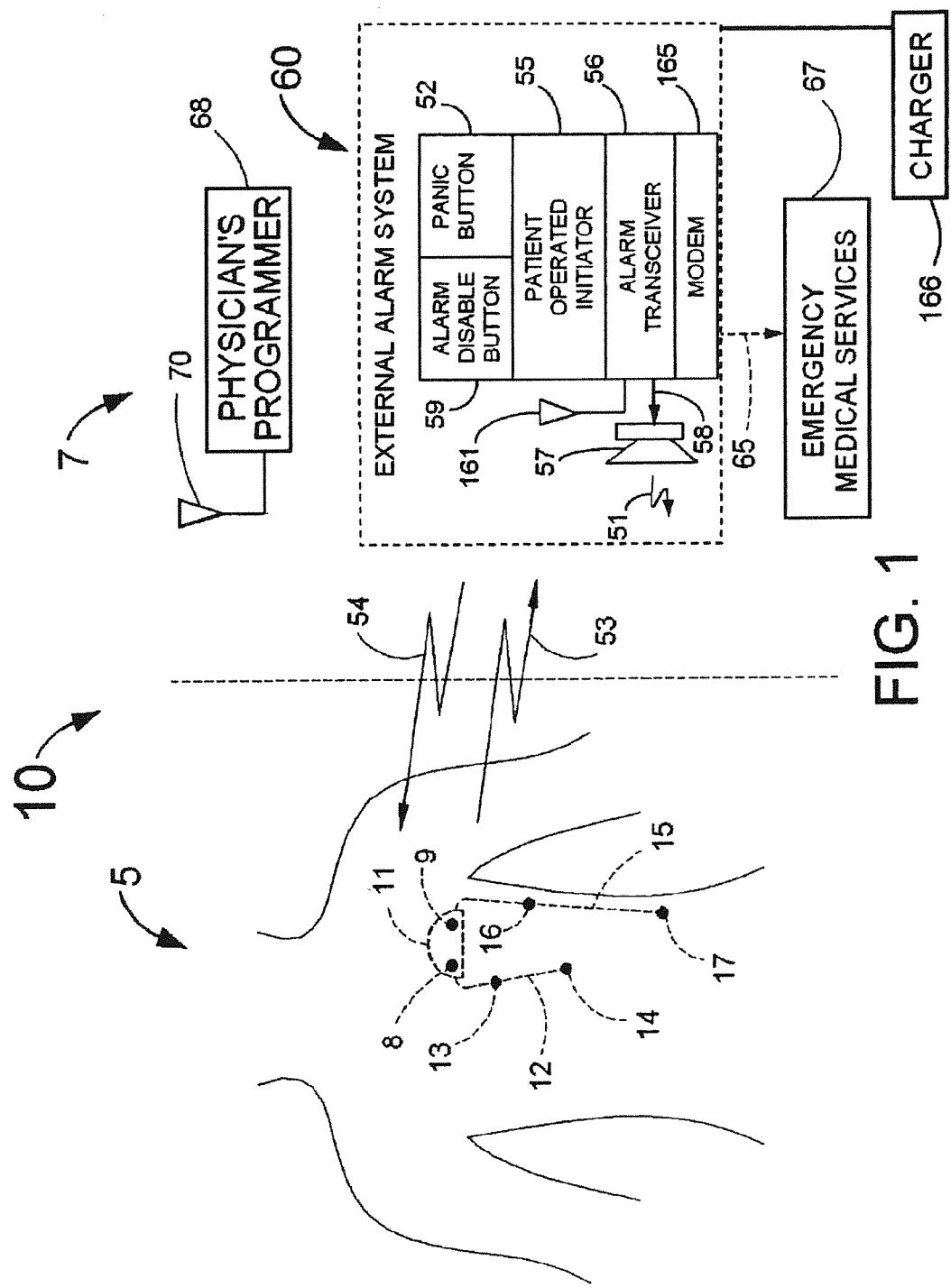
FIG. 1 illustrates a guardian system for the detection of a cardiac event and for warning the patient that a cardiac event is occurring.

FIG. 1 illustrates one embodiment of the guardian system 10 consisting of an implanted cardiosaver 5 and external equipment 7. The battery powered cardiosaver 5 contains electronic circuitry that can detect a cardiac event such as an acute myocardial infarction or arrhythmia and warn the patient when the event occurs. The cardiosaver 5 can store the patient's electrogram for later readout and can send wireless signals 53 to and receive wireless signals 54 from the external equipment 7. The functioning of the cardiosaver 5 will be explained in greater detail with the assistance of FIG. 4.

The cardiosaver 5 has two leads 12 and 15 that have multi-wire electrical conductors with surrounding insulation. The lead 12 is shown with two electrodes 13 and 14. The lead 15 has subcutaneous electrodes 16 and 17. In fact, the cardiosaver 5 could utilize as few as one lead or as many as three and each lead could have as few as one electrode or as many as eight electrodes. Furthermore, electrodes 8 and 9 could be placed on the outer surface of the cardiosaver 5 without any wires being placed externally to the cardiosaver 5.

The lead 12 in FIG. 1 could advantageously be placed through the patient's vascular system with the electrode 14 being placed into the apex of the right ventricle. The lead 12 with electrode 13 could be placed in the right ventricle or right atrium or the superior vena cava similar to the placement of leads for pacemakers and Implantable Coronary Defibrillators (ICDs). The metal case 11 of the cardiosaver 5 could serve as an indifferent electrode with either or both electrodes 13 and/or 14 being active electrodes. It is also conceived that the electrodes 13 and 14 could be used as bipolar electrodes. Alternately, the lead 12 in FIG. 1 could advantageously be placed through the patient's vascular system with the electrode 14 being placed into the apex of the left ventricle. The electrode 13 could be placed in the left atrium.

The lead 15 could advantageously be placed subcutaneously at any location where the electrodes 16 and/or 17 would provide a good electrogram signal indicative of the electrical activity of the heart. Again for this lead 15, the case 11 of the cardiosaver 5 could be an indifferent electrode and the electrodes 16 and/or 17 could be active electrodes or electrodes 16 and 17 could function together as bipolar electrodes. The cardiosaver 5 could operate with only one lead and as few as one active electrode with the case of the cardiosaver 5 being an indifferent electrode. The guardian system 10 described herein can readily operate with only two electrodes.

One embodiment of the cardiosaver device 5 using subcutaneous lead 15 would have the electrode 17 located under the skin on the patient's left side. This could be best located between 2 and 20 inches below the patient's left arm pit. The cardiosaver case 11 could act as the indifferent electrode and would typically be implanted under the skin on the left side of the patient's chest.

FIG. 1 also shows the external equipment 7 that consists of a physician's programmer 68 having an antenna 70, an external alarm system 60 including a charger 166. The external equipment 7 provides means to interact with the cardiosaver 5. These interactions include programming the cardiosaver 5, retrieving data collected by the cardiosaver 5 and handling alarms generated by the cardiosaver 5.

The purpose of the physician's programmer 68 shown in FIG. 1 is to set and/or change the operating parameters of the implantable cardiosaver 5 and to read out data stored in the memory of the cardiosaver 5 such as stored electrogram segments. This would be accomplished by transmission of a wireless signal 54 from the programmer 68 to the cardiosaver 5 and receiving of telemetry by the wireless signal 53 from the cardiosaver 5 to the programmer 68. When a laptop computer is used as the physician's programmer 68, it would require connection to a wireless transceiver for communicating with the cardiosaver 5. Such a transceiver could be connected via a standard interface such as a USB, serial or parallel port or it could be inserted into the laptop's PCMCIA card slot. The screen on the laptop would be used to provide guidance to the physician in communicating with the cardiosaver 5. Also, the screen could be used to display both real time and stored electrograms that are read out from the cardiosaver 5.

In FIG. 1, the external alarm system 60 has a patient operated initiator 55, an alarm disable button 59, a panic button 52, an alarm transceiver 56, an alarm speaker 57 and an antenna 161 and can communicate with emergency medical services 67 with the modem 165 via the communication link 65.

If a cardiac event is detected by the cardiosaver 5, an alarm message is sent by a wireless signal 53 to the alarm transceiver 56 via the antenna 161. When the alarm is received by the alarm transceiver 56 a signal 58 is sent to the loudspeaker 57. The signal 58 will cause the loudspeaker to emit an external alarm signal 51 to warn the patient that an event has occurred. Examples of external alarm signals 51 include a periodic buzzing, a sequence of tones and/or a speech message that instructs the patient as to what actions should be taken. Furthermore, the alarm transceiver 56 can, depending upon the nature of the signal 53, send an outgoing signal over the link 65 to contact emergency medical services 67. When the detection of an acute myocardial infarction is the cause of the alarm, the alarm transceiver 56 could automatically notify emergency medical services 67 that a heart attack has occurred and an ambulance could be sent to treat the patient and to bring him to a hospital emergency room.

If the remote communication with emergency medical services 67 is enabled and a cardiac event alarm is sent within the signal 53, the modem 165 will establish the data communications link 65 over which a message will be transmitted to the emergency medical services 67. The message sent over the link 65 may include any or all of the following information: (1) a specific patient is having an acute myocardial infarction or other cardiac event, (2) the patient's name, address and a brief medical history, (3) a map and/or directions to where the patient is located, (4) the patient's stored electrogram including baseline electrogram data and the specific electrogram segment that generated the alarm (5) continuous real time electrogram data, and (6) a prescription written by the patient's personal physician as to the type and amount of drug to be administered to the patient in the event of a heart attack. If the emergency medical services 67 includes an emergency room at a hospital, information can be transmitted that the patient has had a cardiac event and should be on his way to the emergency room. In this manner the medical practitioners at the emergency room could be prepared for the patient's arrival.

The communications link 65 can be either a wired or wireless telephone connection that allows the alarm transceiver 56 to call out to emergency medical services 67. The typical external alarm system 60 might be built into a Pocket PC or Palm Pilot PDA where the alarm transceiver 56 and modem 165 are built into insertable cards having a standardized interface such as compact flash cards, PCMCIA cards, multimedia, memory stick or secure digital (SD) cards. The modem 165 can be a wireless modem such as the Sierra AirCard 300 or the modem 165 may be a wired modem that connects to a standard telephone line. The modem 165 can also be integrated into the alarm transceiver 56.

The purpose of the patient operated initiator 55 is to give the patient the capability for initiating transmission of the most recently captured electrogram segment from the cardiosaver 5 to the external alarm system 60. This will enable the electrogram segment to be displayed for a medical practitioner. The alarm disable button 59 will turn off the internal alarm signal generated within the cardiosaver 5 and/or the external alarm signal 51 played through the speaker 57.

The patient might press the panic button 52 in the event that the patient feels that he is experiencing a cardiac event. The panic button 52 will initiate the transmission from the cardiosaver 5 to the external alarm system 60 via the wireless signal 53 of both recent and baseline electrogram segments. The external alarm system 60 will then retransmit these data via the link 65 to emergency medical services 67 where a medical practitioner will view the electrogram data.

The remote medical practitioner could then analyze the electrogram data and call the patient back to offer advice as to whether this is an emergency situation or the situation could be routinely handled by the patient's personal physician at some later time.

It is envisioned that there may be preset limits within the external alarm system 60 that prevent the patient operated initiator 55 and/or panic button from being used more than a certain number of times a day to prevent the patient from running down the batteries in the cardiosaver 5 and external alarm system 60 as wireless transmission takes a relatively large amount of power as compared with other functional operation of these devices.

Figure 2:
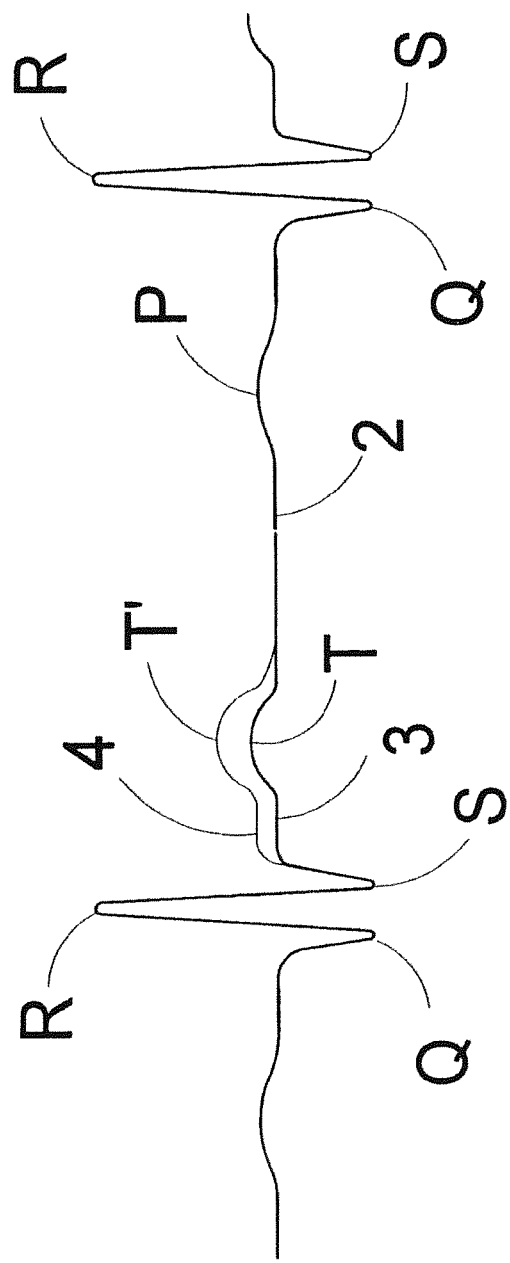
FIG. 2 illustrates a normal electrogram pattern and also shows a superimposed elevated ST segment that would be indicative of an acute myocardial infarction.
Figure 3:
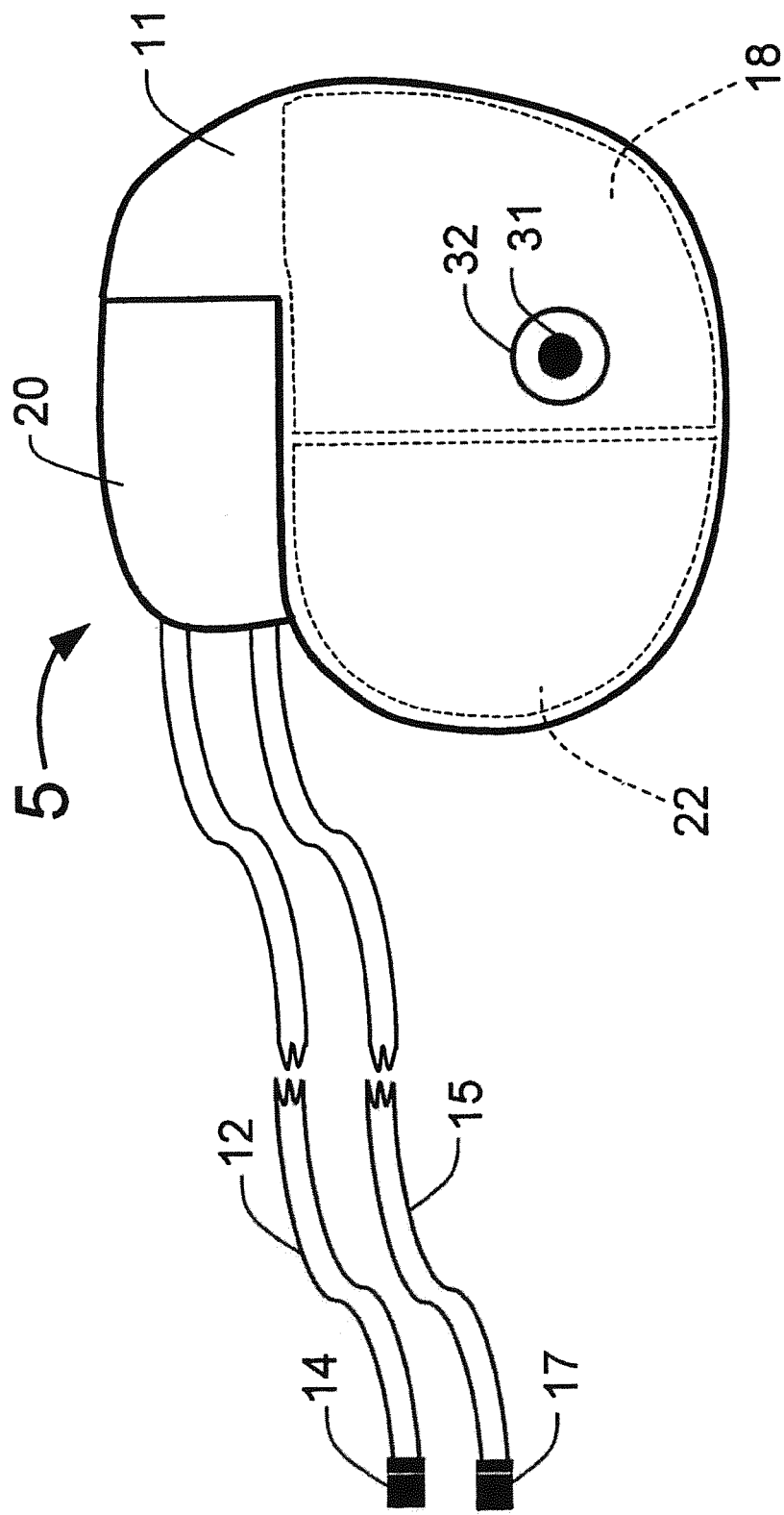
FIG. 3 is a plan view of the cardiosaver showing the cardiosaver electronics module and two electrical leads each having one electrode.

FIG. 2 illustrates a typical electrogram signal from some pair of implanted electrodes such as the electrode 14 and the case 11 of FIG. 3 overlaid with an elevated ST segment 4. The various portions of the electrogram are shown as the P, Q, R, S, and T waves. These are all shown as portions of a heavy solid line in FIG. 2. The normal ST segment 3 is also shown in FIG. 2.

When an acute myocardial infarction occurs, there is typically an elevation (or depression) of the ST segment 4 as shown by the light solid line in FIG. 2. It is this shift of the ST segment 4 as compared to the baseline ST segment 3 that is a clear indicator that an acute myocardial infarction has occurred in a significant portion of the patient's myocardium.

Although an elevated ST segment 4 can be a good indicator of an acute myocardial infarction, other indicators such as a sudden change of heart rate or heart wall motion, intra-coronary blood pressure or a sudden decrease in blood $pO_2$ could also be used as independent sensing means or those signals could be used in addition to the voltage shift of the ST segment 4.

It is important to note that the electrogram from implanted electrodes may provide a faster detection of an ST segment shift as compared to an electrocardiogram signal obtained from skin surface electrodes. Thus the electrogram from implanted electrodes as described herein is the preferred embodiment of the present invention.

It is also well known that the T wave can shift very quickly when a heart attack occurs. It is envisioned that the present invention might detect this T wave shift as compared to a time of 1 to 5 minutes in the past.

It is anticipated that when a patient who has a stenosis in a coronary artery is performing a comparatively strenuous exercise his heart rate increases and he can develop exercise induced ischemia that will also result in a shift of the ST segment of his electrogram. This is particularly true for patients who have undergone balloon angioplasty with or without stent implantation. Such patients will be informed by their own physician that, if their cardiosaver 5 of FIG. 1 activates an alarm during exercise, that it may be indicative of the progression of an arterial stenosis in one of the heart's arteries. Such a patient would be advised to stop all exertion immediately and if the alarm signal goes away as his heart rate slows, the patient should see his doctor as soon as convenient. If the alarm signal does not go away as the patient's heart rate slows down into the normal range then the cardiosaver will change the alarm signal to indicate that the patient should immediately seek medical care. As previously described, the cardiosaver 5 could emit a different signal if there is a heart attack as compared to the signal that would be produced if there were ischemia resulting from exercise.

It is also envisioned that heart rate and the rate of change of heart rate experienced during an ST segment voltage shift can be used to indicate which alarm should be produced by the cardiosaver 5. Specifically, an ST segment shift at a near normal heart rate would indicate an acute myocardial infarction. An ST segment shift when there is an elevated heart rate (e.g., greater than 100 bpm) would generally be indicative of a progressing stenosis in a coronary artery. In any case, if a sufficient ST segment shift occurs that results in an alarm from the cardiosaver 5, the patient should promptly seek medical care to determine the cause of the alarm.

It should be understood that, depending on a patient's medical condition, a vigorous exercise might be as energetic as running a long distance or merely going up a flight of stairs. After the cardiosaver 5 is implanted in a patient who has undergone a stent implant, he should have a stress test to determine his level of ST segment shift that is associated with the highest level of exercise that he can attain. The patient's heart rate should then be noted and the cardiosaver thresholds for detection, described with FIGS. 5 through 9, should be programmed so as to not alarm at ST segment shifts observed during exercise. Then if at a later time the patient experiences an increased shift of his ST segment at that pre-determined heart rate or within a heart rate range, then an alarm indicating ischemia can be programmed to occur. The occurrence of such an alarm can indicate that there is a progression in the narrowing of some coronary artery that may require angiography to determine if angioplasty, possibly including stent implantation, is required.

The alarm signal associated with an excessive ST shift caused by an acute myocardial infarction can be quite different from the "SEE DOCTOR" alarm means associated with progressing ischemia during exercise. For example, the SEE DOCTOR alarm signal might be an audio signal that occurs once every 5 to 10 seconds. A different alarm signal, for example an audio signal that is three buzzes every 3 to 5 seconds, may be used to indicate a major cardiac event such as an acute myocardial infarction. Similar alarm signal timing would typically be used for both internal alarm signals generated by the alarm sub-system 48 of FIG. 4 and external alarm signals generated by the external alarm system 60.

In any case, a patient can be taught to recognize which signal occurs for these different circumstances so that he can take immediate response if an acute myocardial infarction is indicated but can take a non-emergency response if progression of the narrowing of a stenosis or some other less critical condition is indicated. It should be understood that other distinctly different audio alarm patterns could be used for different arrhythmias such as atrial fibrillation, atrial flutter, PVC's, PAC's, etc. A capability of the physician's programmer 68 of FIG. 1 would be to program different alarm signal patterns, enable or disable detection and/or generation of associated alarm signals in the cardiosaver for any one or more of these various cardiac events. Also, the intensity of the audio alarm, vibration or electrical tickle alarm could be adjusted to suit the needs of different patients. In order to familiarize the patient with the different alarm signals, the programmer 68 of the present invention would have the capability to turn each of the different alai in signals on and off.

FIG. 3 is a plan view of the cardiosaver 5 having a case 11 and a plastic header 20. The case 11 contains the battery 22 and the electronics module 18. This type of package is well known for pacemakers, implantable defibrillators and implantable tissue stimulators. Electrical conductors placed through the plastic header 20 connect the electronics module 18 to the electrical leads 12 and 15, which have respectively electrodes 14 and 17. The on-case electrodes 8 and 9 of FIG. 1 are not shown in FIG. 3. It should also be understood that the cardiosaver 5 can function with only two electrodes, one of which could be the case 11. All the different configurations for electrodes shown in FIGS. 1 and 3, such as the electrodes 8, 9, 13, 14, 16 or the metal case 11 are shown only to indicate that there are a variety of possible electrode arrangements that can be used with the cardiosaver 5.

On the metal case 11, a conducting disc 31 mounted onto an insulating disc 32 can be used to provide a subcutaneous electrical tickle to warn the patient that an acute myocardial infarction is occurring or to act as an independent electrode.

Figure 4:
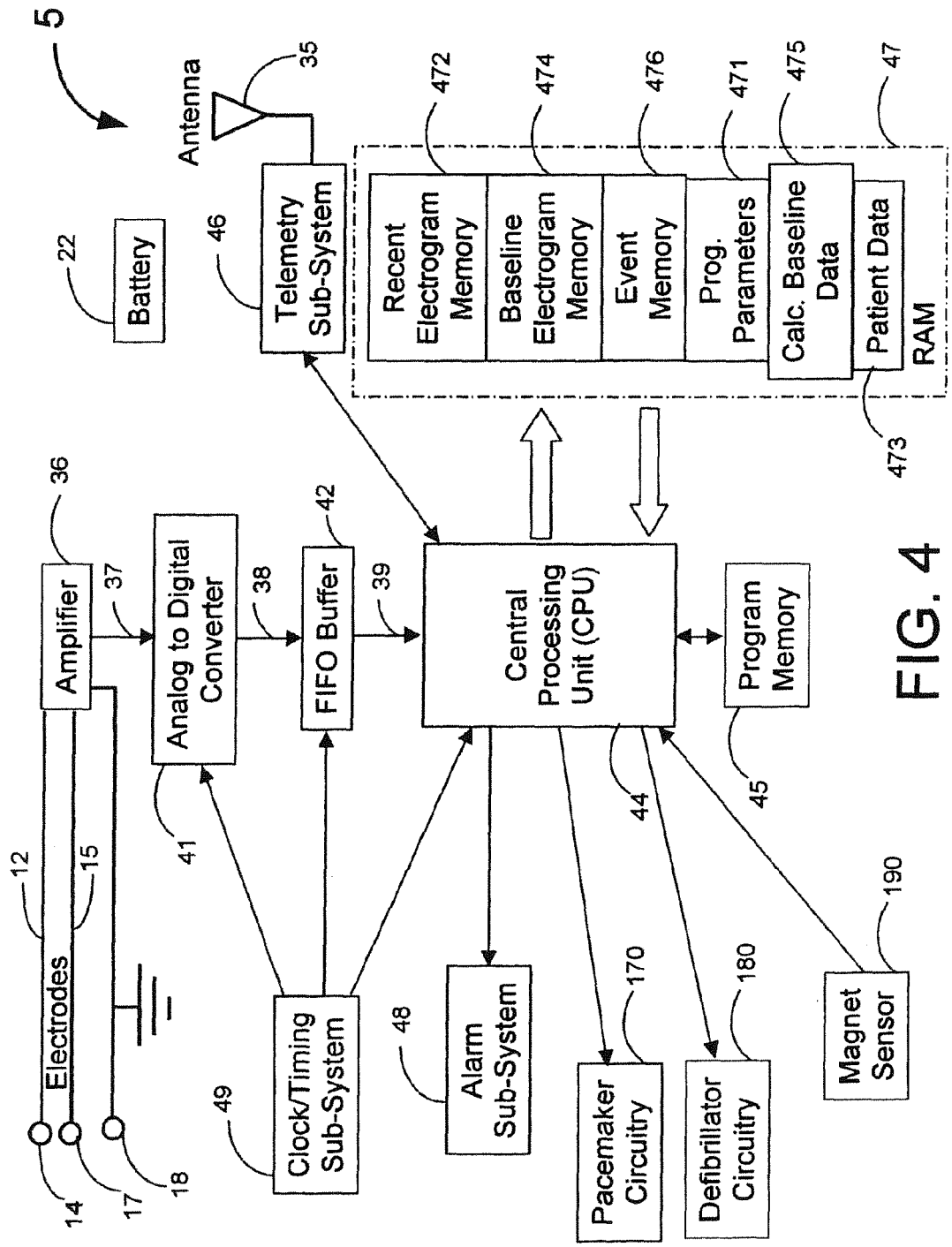
FIG. 4 is a block diagram of the cardiosaver.

FIG. 4 is a block diagram of the cardiosaver 5 with battery 22. The electrodes 14 and 17 connect with wires 12 and 15 respectively to the amplifier 36 that is also connected to the case 11 acting as an indifferent electrode. As two or more electrodes 12 and 15 are shown here, the amplifier 36 would be a multi-channel amplifier. The amplified electrogram signals 37 from the amplifier 36 are then converted to digital signals 38 by the analog-to-digital converter 41. The digital electrogram signals 38 are buffered in the First-In-First-Out (FIFO) memory 42. Processor means shown in FIG. 4 as the central processing unit (CPU) 44 coupled to memory means shown in FIG. 4 as the Random Access Memory (RAM) 47 can process the digital electrogram data 38 stored the FIFO 42 according to the programming instructions stored in the program memory 45. This programming (i.e. software) enables the cardiosaver 5 to detect the occurrence of a cardiac event such as an acute myocardial infarction.

A clock/timing sub-system 49 provides the means for timing specific activities of the cardiosaver 5 including the absolute or relative time stamping of detected cardiac events. The clock/timing sub-system 49 can also facilitate power savings by causing components of the cardiosaver 5 to go into a low power standby mode in between times for electrogram signal collection and processing. Such cycled power savings techniques are often used in implantable pacemakers and defibrillators. In an alternate embodiment, the clock/timing sub-system can be provided by a program subroutine run by the central processing unit 44.

In an advanced embodiment of the present invention, the clock/timing circuitry 49 would count for a first period (e.g. 20 seconds) then it would enable the analog-to-digital converter 41 and FIFO 42 to begin storing data, after a second period (e.g. 10 seconds) the timing circuitry 49 would wake up the CPU 44 from its low power standby mode. The CPU 44 would then process the 10 seconds of data in a very short time (typically less than a second) and go back to low power mode. This would allow an on off duty cycle of the CPU 44 which often draws the most power of less than 2 seconds per minute while actually collecting electrogram data for 20 seconds per minute.

In a preferred embodiment of the present invention the RAM 47 includes specific memory locations for 3 sets of electrogram segment storage. These are the recent electrogram storage 472 that would store the last 2 to 10 minutes of recently recorded electrogram segments so that the electrogram data leading in the period just before the onset of a cardiac event can be reviewed at a later time by the patient's physician using the physician's programmer 68 of FIG. 1. For example, the recent electrogram storage 472 might contain eight 10 second long electrogram segments that were captured every 30 seconds over the last 4 minutes.

The baseline electrogram memory 474 would provide storage for baseline electrogram segments collected at preset times over one or more days. For example, the baseline electrogram memory 474 might contain 24 baseline electrogram segments of 10 seconds duration, one from each hour for the last day.

The event memory 476 occupies the largest part of the RAM 47. The event memory 476 is not overwritten on a regular schedule as are the recent electrogram memory 472 and baseline electrogram memory 474 but is typically maintained until read out by the patient's physician with the programmer 68 of FIG. 1. At the time a cardiac event like excessive ST shift indicating an acute myocardial infarction is detected by the CPU 44, all (or part) of the entire contents of the baseline and recent electrogram memories 472 and 474 would typically be copied into the event memory 476 so as to save the pre-event data for later physician review.

The RAM 47 also contains memory sections for programmable parameters 471 and calculated baseline data 475. The programmable parameters 471 include the upper and lower limits for the normal and elevated heart rate ranges, and physician programmed parameters related to the cardiac event detection processes stored in the program memory 45. The calculated baseline data 475 contain detection parameters extracted from the baseline electrogram segments stored in the baseline electrogram memory 474. Calculated baseline data 475 and programmable parameters 471 would typically be saved to the event memory 476 following the detection of a cardiac event. The RAM 47 also includes patient data 473 that may include the patient's name, address, telephone number, medical history, insurance information, doctor's name, and specific prescriptions for different medications to be administered by medical practitioners in the event of different cardiac events.

It is envisioned that the cardiosaver 5 could also contain pacemaker circuitry 170 and/or defibrillator circuitry 180 similar to the cardiosaver systems described by Fischell in U.S. Pat. No. 6,240,049.

The alarm sub-system 48 contains the circuitry and transducers to produce the internal alarm signals for the cardiosaver 5. The internal alarm signal can be a mechanical vibration, a sound or a subcutaneous electrical tickle or shock.

The telemetry sub-system 46 with antenna 35 provides the cardiosaver 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiosaver 5. It is also envisioned that standard wireless protocols such as Bluetooth and 802.11a or 802.11b might be used to allow communication with a wider group of peripheral devices.

A magnet sensor 190 may be incorporated into the cardiosaver 5. An important use of the magnet sensor 190 is to turn on the cardiosaver 5 on just before programming and implantation. This would reduce wasted battery life in the period between the times that the cardiosaver 5 is packaged at the factory until the day it is implanted.

Figure 5:
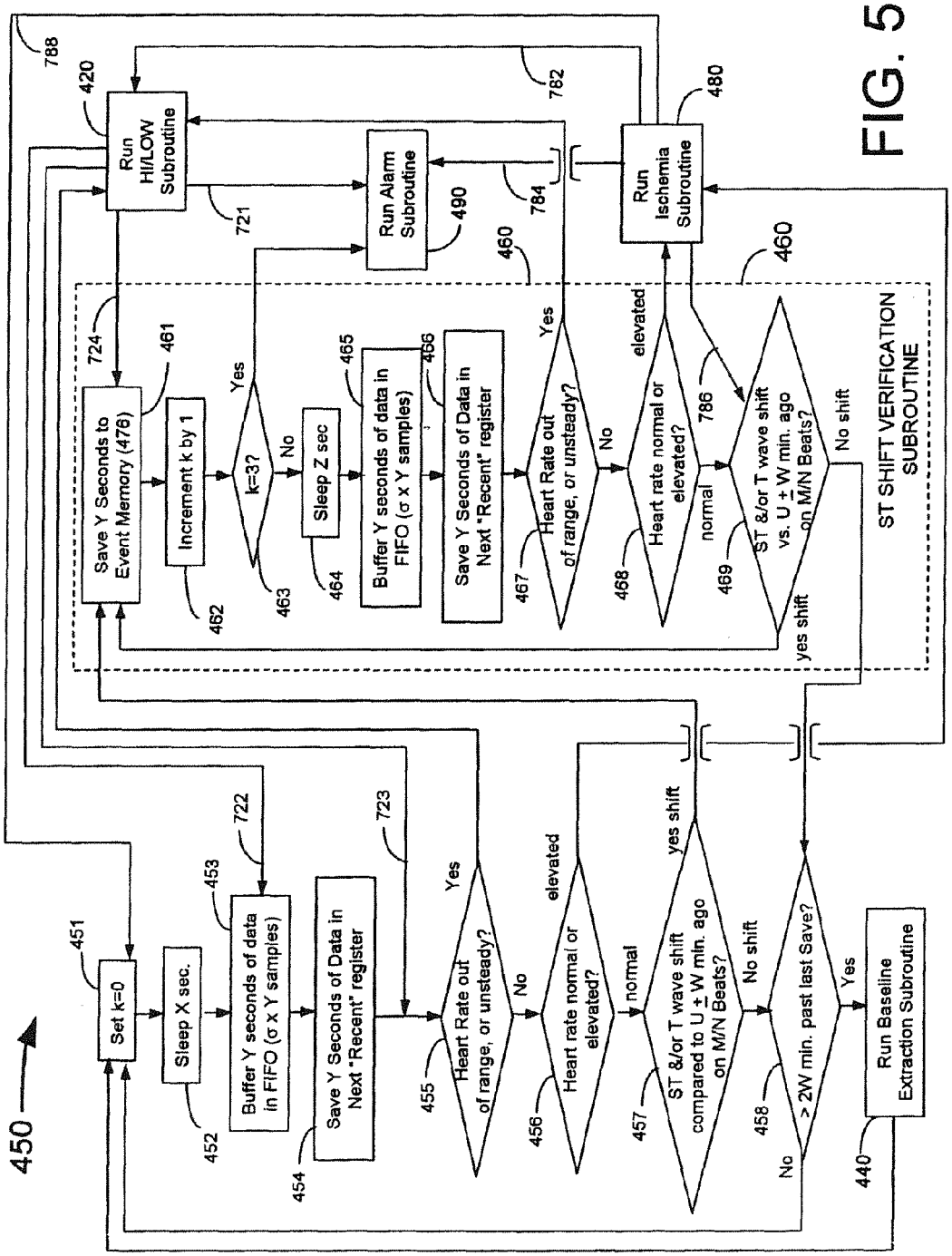
FIG. 5 is a block diagram of the cardiosaver event detection program.

FIG. 5 illustrates in the form of a block diagram the operation of the heart signal processing program 450 for cardiac event detection by the cardiosaver 5 of FIGS. 1-4. The heart signal processing program 450 is an example of one of many such detection programs whose instructions could reside in the program memory 45 for use by the CPU 44 of the cardiosaver 5 as shown in FIG. 4. The main section of the heart signal processing program 450 begins with step 451 where the event counter "k" is set to zero indicating there have been no detected events. Next, in step 452 the cardiosaver 5 is said to sleep for X seconds. The term sleep here indicates that for a period of X seconds, the cardiosaver 5 would either be placed in a low power standby mode (if available) or would otherwise simply wait for a time of X seconds before moving to step 453. Step 453 following 452 has an electrogram segment representing Y seconds of electrogram data captured into the FIFO buffer 42 of FIG. 4. $\sigma$ is the data sampling rate in samples per second, thus the total number of samples collected in step 453 is a multiplied by Y. It is envisioned that X would be a time between 5 seconds and 5 minutes with 20 seconds as a preferred value. Y would be between 3 and 30 seconds with 10 seconds as a preferred value. $\sigma$ is typically between 100 and 500 samples per second with 200 samples per second being a preferred value.

After being captured, in step 454, the Y seconds of electrogram data representing the most recent electrogram segment is transferred to the recent electrogram memory 472 of FIG. 4. At this time the processing and analysis of the data begins. Throughout the remainder of this detailed description of the drawings, the "Y second long electrogram segment" refers to the most recently collected Y seconds of electrogram data that have been captured and transferred to the recent electrogram memory 472 by the steps 453 and 454. The term "recent electrogram segments" refers to all of the electrogram segments stored in the recent electrogram memory 472. For example, there could be eight total 10 second long recent electrogram segments that were captured at 30 second intervals over a 4 minute period.

The first processing step following the collection of the Y second long electrogram segment is step 455 that measures the intervals between the R waves in the most Y second long electrogram segment. These R-R intervals are then used to calculate the average heart rate and R-R interval variation for the Y second long electrogram segment. If the average heart rate is below a programmed low heart rate limit $\rho_{low}$ or above a programmed high heart rate limit $\rho_{high}$, it is considered "out-of-range" and a Hi/Low heart rate subroutine 420 (see FIG. 9) is run to properly respond to the condition.

If the R-R interval variation within the Y second long electrogram segment is more than a programmed limit, the hi/low heart rate subroutine is also run. This is an important feature of the present invention as PVC's and unstable heart rhythms such as a bigeminal rhythm can cause errors in an ST shift detection algorithm that is works best with a steady heart rhythm. One embodiment of the present invention identifies an unsteady heart rate by comparing the two shortest R-R intervals and the 2 longest intervals in the Y second long electrogram segment. If the difference between both of the two shortest R-R intervals and the average of the two longest R-R intervals are more than a programmed percentage $\alpha$, an unsteady heart rate is identified. For example the programmed percentage $\alpha\square$ might be 25% so that if the two shortest R-R intervals are each more than 25% less than the average of the two longest R-R intervals, then the heart rate is unsteady. It is envisioned that if longer times Y are used for electrogram segment collection then it might require 3 or more "short" beats to indicated an unsteady heart rate. Any beat that is not too short is classified by step 455 as a normal beat. $\rho_{low}$, $\rho_{high}$ and $\alpha$ are programmable parameters typically set using the programmer 68 during programming of the cardiosaver 5. Typical values for $\rho_{low}$ and $\rho_{high}$ would be 50 and 140 beats per minute respectively.

Figure 10:
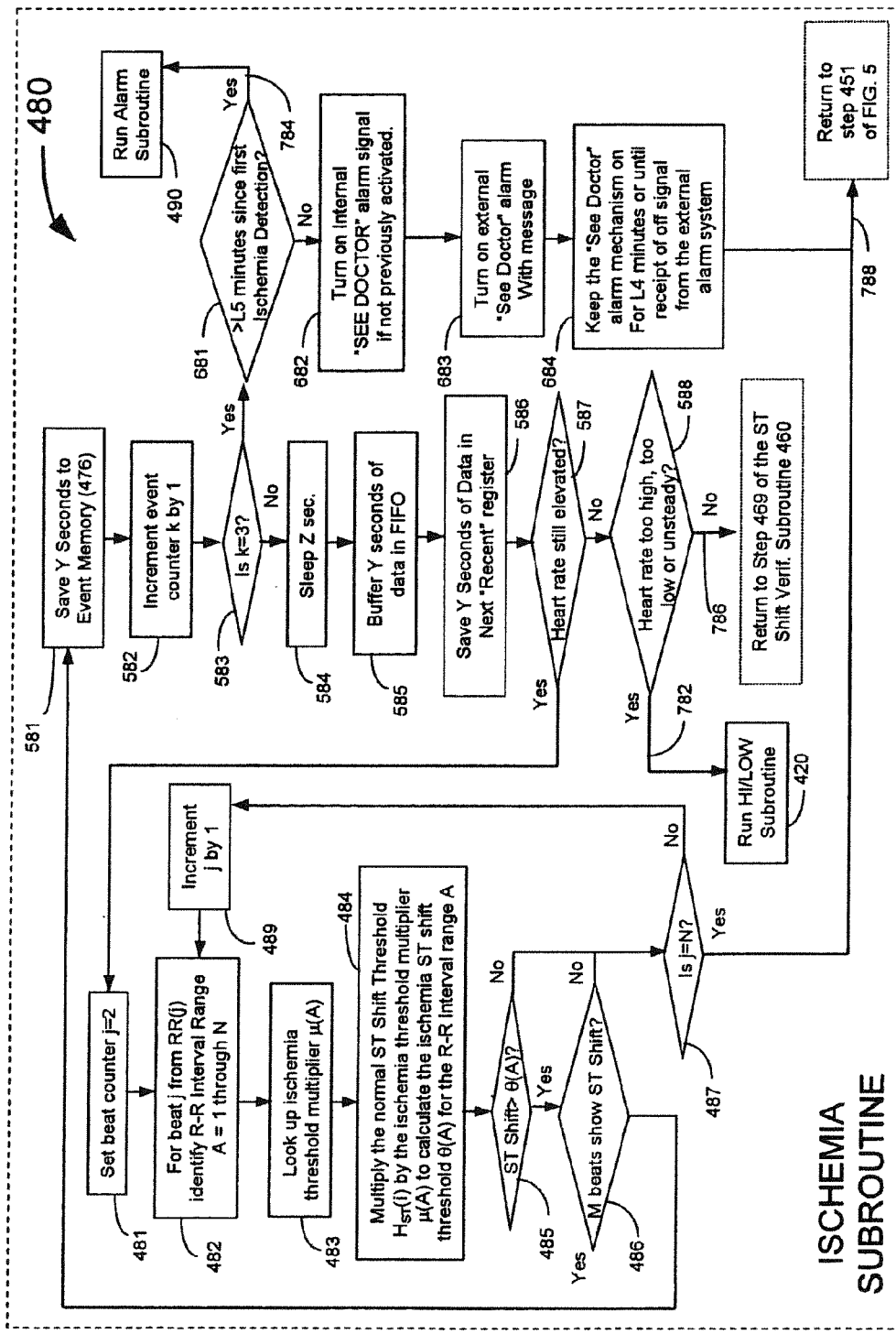
FIG. 10 is a block diagram of the ischemia subroutine of the cardiosaver event detection program

If the heart rate is not high, low or unsteady as checked in step 455, the heart signal processing program 450 moves to step 456 where the average heart rate is compared to a programmed normal range between $\rho_{low}$ and $\rho_{elevated}$ where $\rho_{elevated}$ is the elevated heart rate limit that defines the upper limit of the "normal range" (e.g. 80 beats per minute). If the patient's heart rate is elevated but not out-of-range (i.e. above $\rho_{high}$), the patient may be exercising and the ischemia subroutine 480 allows for different cardiac event detection criteria during elevated heart rates to reduce false positive detections of acute myocardial infarction and to detect exercise induced ischemia. An example of one embodiment of the ischemia subroutine 480 is illustrated in FIG. 10.

Although the above specification describes low, high and elevated heart rate limits $\rho_{low}$, $\rho_{high}$ and $\rho_{elevated}$, it is envisioned that instead of heart rate (i.e. beats per second) the limits and decision making could be set in terms or R wave to R wave (R-R) interval with the low, high and elevated limits are for R-R interval and are expressed in seconds per beat, milliseconds per beat or samples per beat.

If the average heart rate of the patient is within the "normal" range in step 456, then the program 450 moves to step 457 where it looks for an excessive ST shift on M out of N beats as compared with the baseline electrogram segment collected at a time U±W minutes in the past. U can be any time from 1 minute to 48 hours but to allow for daily cycles U=24 hours is a preferred embodiment. W is half the interval between times when the baseline data is saved and can be any time from 10 seconds to 12 hours. For a U of 24 hours, a preferred setting would have W equal to half an hour so that the current Y second long electrogram segment is always being compared with a baseline electrogram segment from 24±½ hour before. This also means that baseline electrogram segments are saved and processed to extract detection parameters at an interval of twice W (2 W). I.e., if W is half an hour, then the baseline data is saved and processed once an hour. M can be any number from 1 to 30 and N can be any number from M to 100. An example of a typical M and N used would be 6 out of 8 beats. It is envisioned that the first of the 8 beats will typically be the beat including the $2^{nd}$ R wave in the Y second long electrogram segment collected in steps 453 and 454.

If one is trying to detect abnormalities in 6 out of 8 beats for a positive detection, a negative detection will occur whenever 3 normal beats without a detected abnormality are found (so long as it is before the 6 "abnormal" beats with detected abnormalities). To save processing time and potentially extend battery life it is desirable to have steps 457 and 469 of FIG. 5 simultaneously count both the number of normal beats and the number of abnormal beats. The steps 457 and 469 will stop processing beats when either 3 normal beats (a negative detection) or 6 abnormal beats (a positive detection) are found. Another advantage of this technique is that even if the Y second long electrogram segments collected in steps 453 and 465 have less than 6 beats but there are at least 3 normal beats, there is sufficient data to declare a negative detection (i.e. nothing is wrong). As heart attacks occur rarely, this improvement will greatly enhance the efficiency of detection algorithm. Although the example above uses 3 normal vs. 6 out of 8 abnormal beats, this technique will work for any M out of N detection scheme where N−M+1 normal beats is sufficient to declare that no event has occurred. This enhancement will work in any device for detecting cardiac events whether implanted within the patient or external to the patient. This technique both looking for normal and abnormal beats can be applied throughout the subroutines of the present invention. For example, ST shift is detected in steps 434 and 439 of FIG. 9 and is of particular importance with a low heart rate where there may not be M beats to process in the Y seconds. It is also applicable to the Unsteady Heart Rate Subroutine 410 in step 418 and can reduce the number of times that an additional Y second electrogram segment must be collected to get sufficient data to detect the presence or absence of an event.

Figure 12:
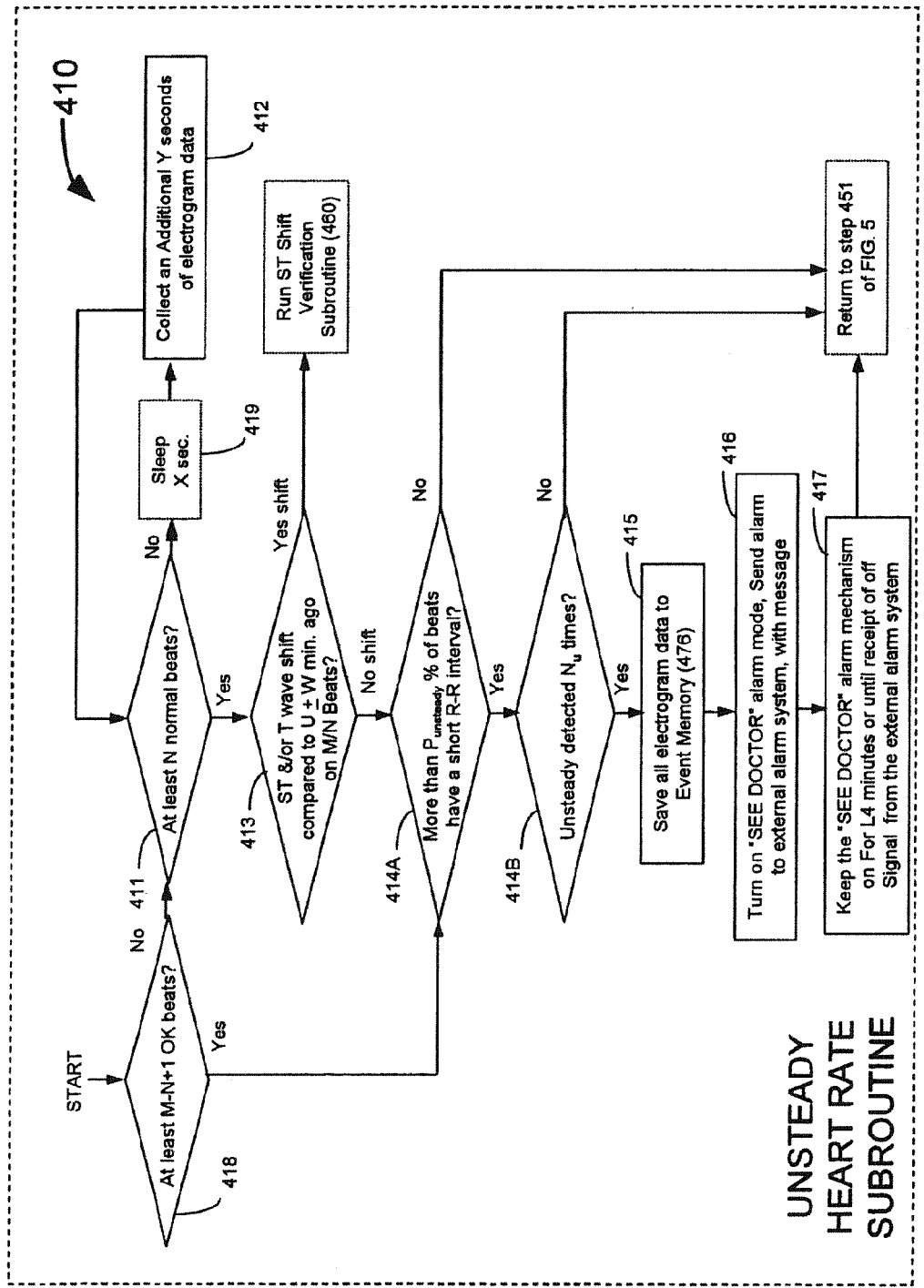
FIG. 12 is a block diagram of the unsteady heart rate subroutine of the cardiosaver event detection program.

The electrogram segment length Y should be programmed to be of sufficient length such that there will be more than N beats within the Y second electrogram segment for heart rates at the low limit for the normal heart rate range. If Y is too short, then the programs 450 and 460 may need to also allow for the collection of additional electrogram data as shown in FIG. 12 for the unsteady heart rate subroutine 410.

An alternate to ST shift detection in step 457 is to process just the T wave, which can change its peak or average amplitude rapidly if there is a heart attack. The T wave can, however change its amplitude slowly under normal conditions so a T wave shift detector would need a much shorter time U than that of a detector using the ST segment before the T wave. If the detector is checking for such T wave shift, i.e. a voltage shift of the T wave part of the ST segment, then it may be desirable to check against a baseline where U is 1 to 30 minutes and W is 15 seconds to 15 minutes. For example, U=3 minutes and W=15 seconds is a preferred setting to catch a quickly changing T wave. This would also allow use of recent electrogram segments stored in the recent electrogram memory of FIG. 4 as baseline electrogram segments for T wave shift detection. It is envisioned that the programmer 68 of FIG. 1 would allow the patient's doctor to program the cardiosaver 5 to use ST segment shift or T wave shift detectors by themselves, or together simultaneously. If both were used then the programmer 68 would allow the patient's doctor to choose whether a positive detection will result if either technique detects an event or only if both detect an event.

Figure 7:
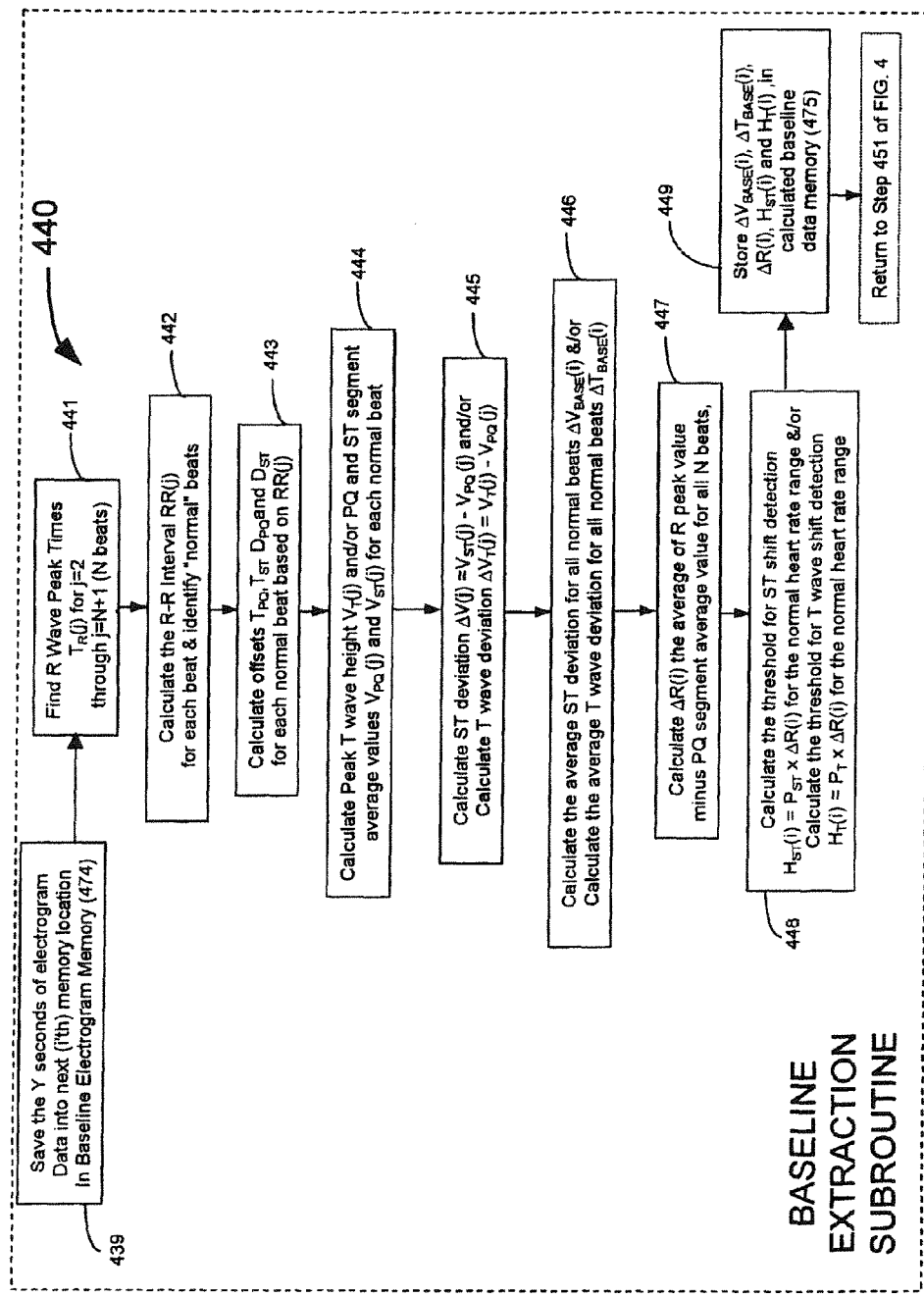
FIG. 7 is a block diagram of the baseline parameter extraction subroutine of the cardiosaver event detection program.

If the average heart rate is in the normal range, is not unsteady and there is no cardiac event detection in step 457, (i.e. the electrogram signal is indicative of a "normal" heart signal for the patient), the heart signal processing program 450 checks in step 458 if it is more than the interval of 2 W minutes since the last time baseline data was captured. If it has been more than 2 W, the baseline parameter extraction subroutine 440 of FIG. 7 is run.

The parameters X, Y, U and W are stored with the programmable parameters 471 in the RAM 47 in FIG. 4. These parameters may be permanently set at the time of manufacturing of the cardiosaver 5 or they may be programmed through the programmer 68 of FIG. 1. The calculated criteria for cardiac event detection extracted from the baseline electrogram segments stored in baseline electrogram memory 474 are stored in the calculated baseline data memory 475 of the RAM 47.

A typical configuration of the heart signal processing program 450 using only an ST shift detector, would use a sleep of X=20 seconds, followed by collection of a Y=10 second long electrogram segment. If the patient's heart rate is in a normal range of between 50 and 80 beats per minute, step 457 would check for an excessive shift of the ST segment in 6 out of 8 of the beats as compared with baseline data collected 24±½ hour previously.

If there has been a detected excessive ST shift in M out of N beats in step 457, the ST Verification Subroutine 460 is run to be sure that the detected event is not a transitory change in the electrogram.

The ST Verification Subroutine 460 begins with step 461 where the recently collected Y second long electrogram segment is saved to the event memory 476 of FIG. 4 for later review by the patient's doctor.

Figure 8:
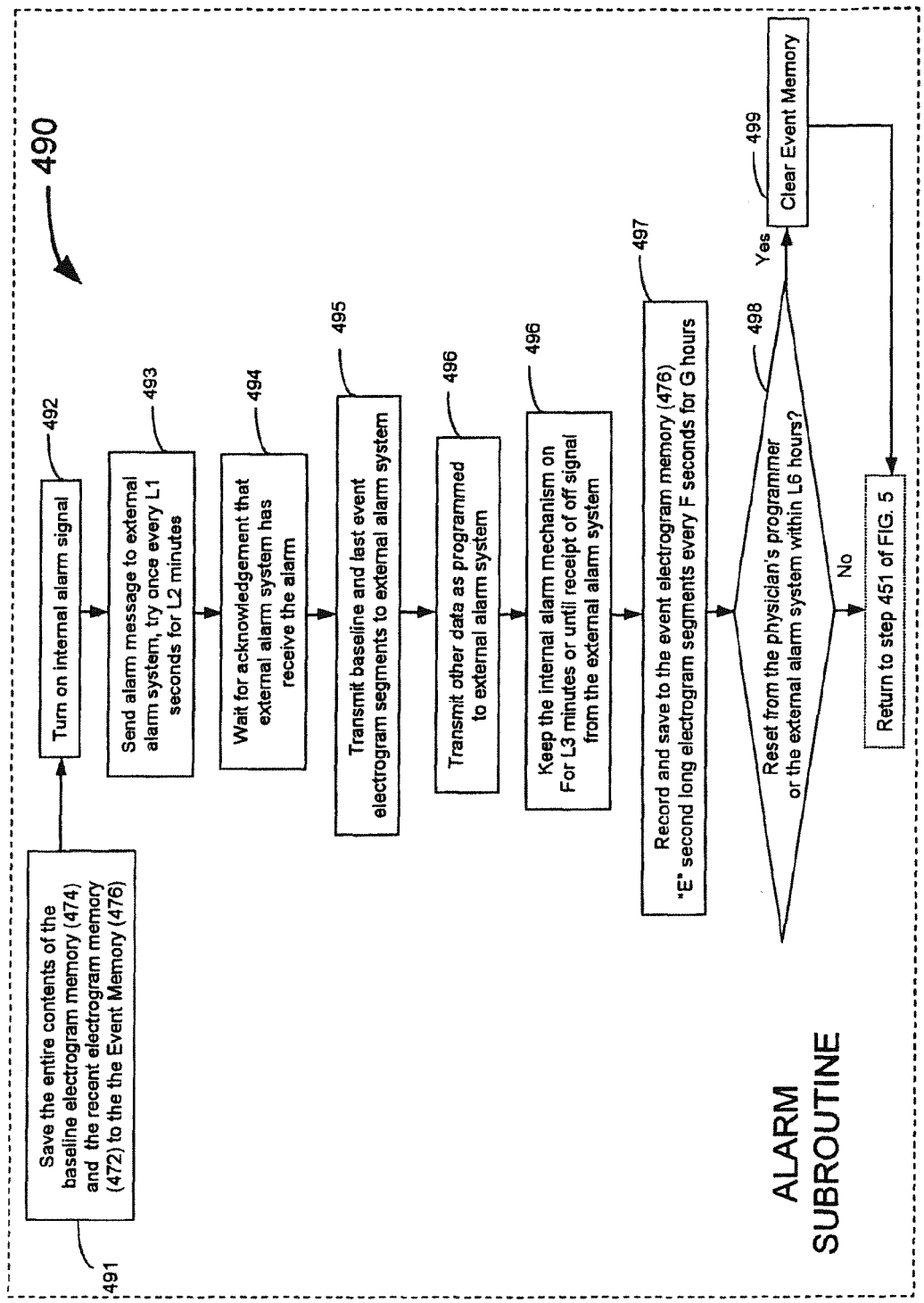
FIG. 8 is a block diagram of the alarm subroutine of the cardiosaver event detection program.
Figure 11:
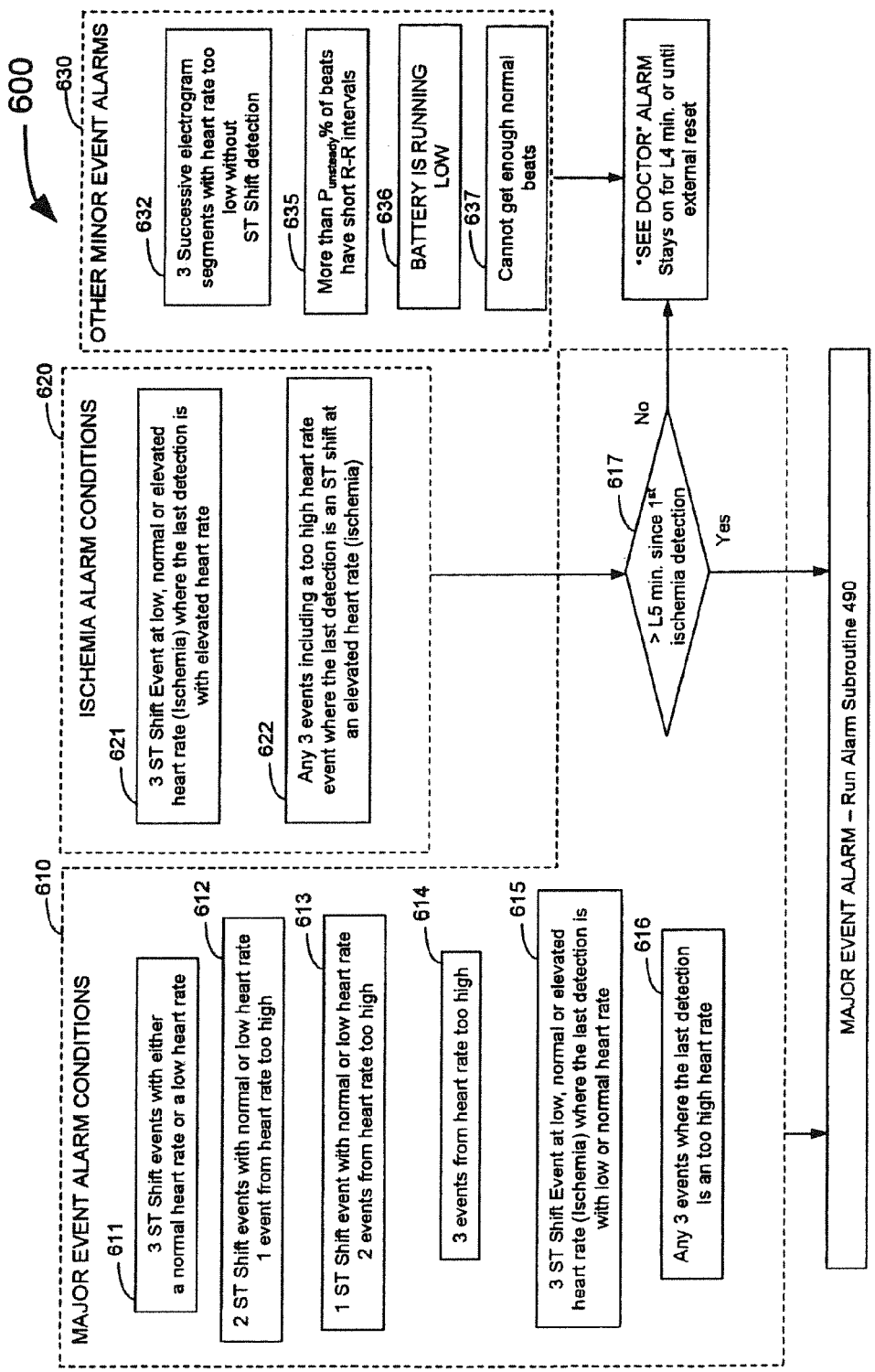
FIG. 11 is a diagram of the conditions that trigger cardiosaver alarms.

The ST shift verification subroutine 460 then increments the event counter k by 1 (step 462) and then checks (step 463) if k is equal to 3 (i.e. 3 events is the trigger for an alarm. If k=3 then the alarm subroutine 490 illustrated in FIG. 8 is run, thus declaring that there has been a positive detection of a major cardiac event. FIG. 11 illustrates examples of the combinations of conditions that can lead to k=3 and the running of the alarm subroutine 490.

Although step 463 is shown checking if k=3 as the condition for running the alarm subroutine 490, the number of events required could be a programmable parameter from k=1 to k=20. Even higher possible values than k=20 might be used to avoid false positive detections. With current average times from onset of a heart attack to arrival at a treatment center of 3 hours, a few minutes delay for a device that should enable the patient to easily reach a treatment center within 30 minutes is valuable if it improves the reliability of detection.

In step 463 if k is less than 3 then the ST shift verification subroutine 460 proceeds to sleep Z seconds in step 464 followed by collection (step 465) and saving (step 466) to the next location in the recent electrogram memory 472 of FIG. 4 of a new Y second long electrogram segment. Z seconds can be different from the X seconds used in step 452 to allow the ST shift verification subroutine 460 to look over longer (or shorter) intervals than the main program so as to best verify the positive detection of step 457. The term sleep here has the same connotation as in step 452. A preferred embodiment of the present invention uses Z=X=20 seconds.

The ST shift verification subroutine 460 then checks for heart rate out-of-range or unsteady in step 467. As described with respect to step 455 above, heart rate out-of-range means that the average heart rate in the Y second long electrogram segment is below the low heart rate limit $\rho_{low}$ or above the high heart rate limit $\rho_{high}$.

If the heart rate is out-of range or unsteady step 467 will initiate the Hi/Low subroutine 420. If the heart rate is not out-of range or unsteady, then step 468 follows to check if the heart rate is normal or elevated similar to step 456 above. If the heart rate is elevated, the ischemia subroutine 480 is run. The reason for checking if the heart rate has changed is that acute myocardial infarction can induce high heart rates from tachycardia or fibrillation that might mask the ST shift but are in of themselves major cardiac events whose detection will increment the event counter k.

If the heart rate is in the normal range (i.e. not elevated), then step 469 checks for an excessive ST and/or T wave shift in M out of N beats of the Y second long electrogram segment as compared with the baseline data extracted U±W minutes in the past (similar to step 457). If no excessive ST and/or T wave shift is seen, the subroutine 460 returns to step 458 of the heart signal processing program 450 and then eventually back to step 451, the start of heart signal processing program 450. In step 451, k is set back to 0 so that only if there are cardiac events detected in three (k) successive Y second long electrogram segments, will the alarm subroutine 490 be run. In a preferred embodiment of the present invention, steps 457 and 469 only examine M out of N "normal" beats, ignoring any beats that are too short as determined by step 455.

It is important to note, that baseline data is extracted only when the heart rate is within the normal range and there is not an excessive ST or T wave shift in M out of N beats. In one embodiment of the present invention, this is improved further by having the baseline parameter extraction subroutine 440 only process normal beats that individually do not exhibit an excessive ST and/or T wave shift.

Figure 6:
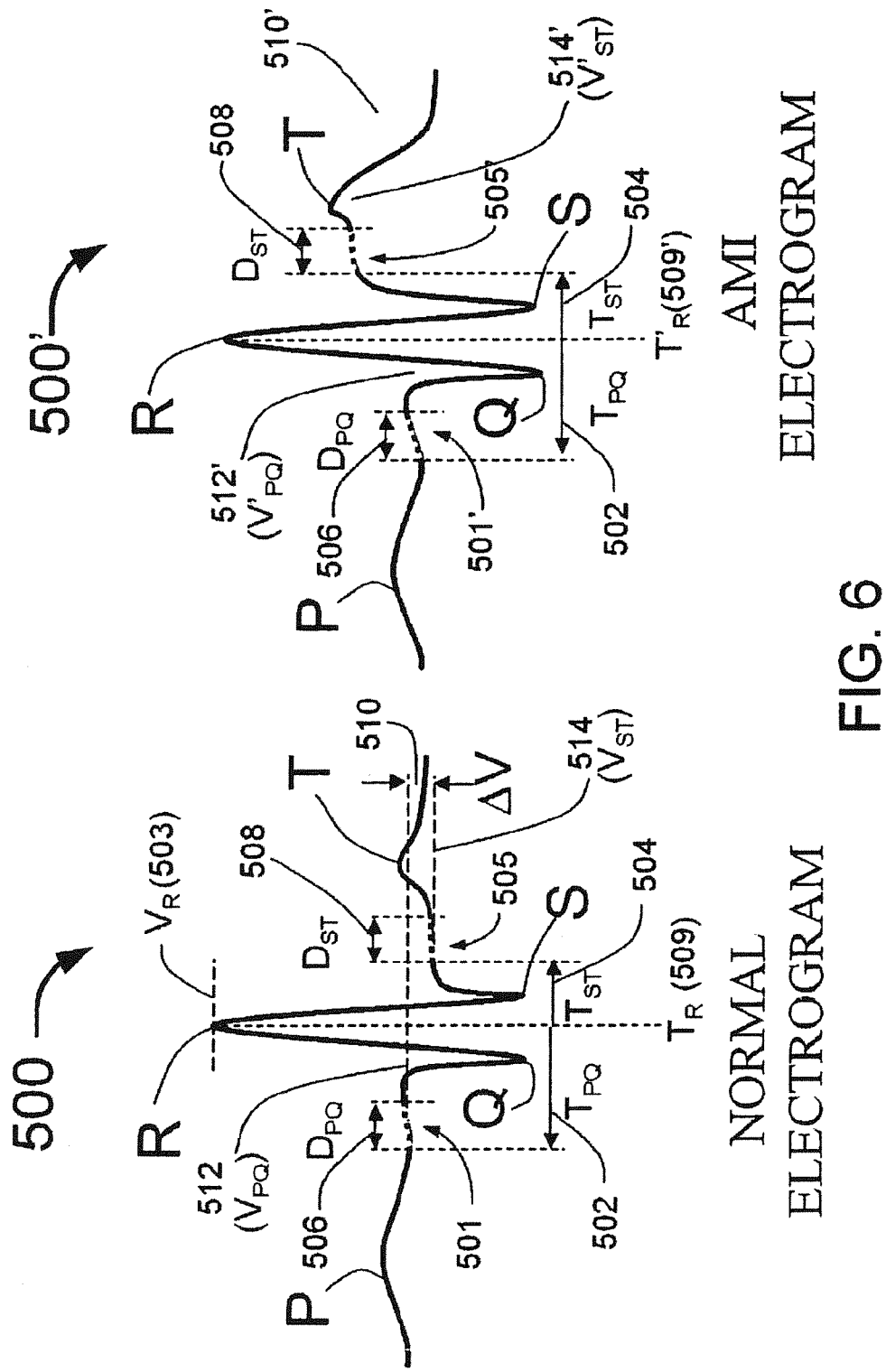
FIG. 6 illustrates the extracted electrogram segment features used to calculate ST shift.

FIG. 6 illustrates the features of a single normal beat 500 of an electrogram segment and a single beat 500' of an AMI electrogram segment that has a significant ST segment shift as compared with the normal beat 500. Such ST segment shifting occurs within minutes following the occlusion of a coronary artery during an AMI. The beats 500 and 500' show typical heart beat wave elements labeled P, Q, R, S, and T. The definition of a beat such as the beat 500 is a sub-segment of an electrogram segment containing exactly one R wave and including the P and Q elements before the R wave and the S and T elements following the R wave.

For the purposes of detection algorithms, different sub-segments, elements and calculated values related to the beats 500 and 500' are hereby specified. The peak of the R wave of the beat 500 occurs at the time $T_R$ (509). The PQ segment 501 and ST segment 505 are sub-segments of the normal beat 500 and are located in time with respect to the time $T_R$ (509) as follows:

a. The PQ segment 501 has a time duration $D_{PQ}$ (506) and starts $T_{PQ}$ (502) milliseconds before the time $T_R$ (509).

b. The ST segment 505 has a time duration $D_{ST}$ (508) and starts $T_{ST}$ (502) milliseconds after the time $T_R$ (509).

The PQ segment 501' and ST segment 505' are sub-segments of the beat 500' and are located in time with respect to the time $T'_R$ (509') as follows:

c. The PQ segment 501' has a time duration $D_{PQ}$ (506) and starts $T_{PQ}$ (502) milliseconds before the time $T'_R$ (509').

d. The ST segment 505' has a time duration $D_{ST}$ (508) and starts $T_{ST}$ (502) milliseconds after the time $T'_R$ (509').

The ST segments 505 and 505' and the PQ segments 501 and 501' are examples of sub-segments of the electrical signals from a patient's heart. The R wave and T wave are also sub-segments. The dashed lines $V_{PQ}$ (512) and $V_{ST}$ (514) illustrate the average voltage amplitudes of the PQ and ST segments 501 and 505 respectively for the normal beat 500. Similarly the dashed lines $V'_{PQ}$ (512') and $V'_{ST}$ (514') illustrate the average amplitudes of the PQ and ST segments 501' and 505' respectively for the beat 500'. The "ST deviation" $\Delta V$ (510) of the normal beat 500 and the ST deviation $\Delta V_{AMI}$ (510') of the AMI electrogram beat 500' are defined as:

$$\Delta V(510) = V_{ST}(514) - V_{PQ}(512)$$

$$\Delta V_{AMI}(510') = V'_{ST}(514') - V'_{PQ}(512')$$

Note that the both beats 500 and 500' are analyzed using the same time offsets $T_{PQ}$ and $T_{ST}$ from the peak of the R wave and the same durations $D_{PQ}$ and $D_{ST}$. In this example, the beats 500 and 500' are of the same time duration (i.e. the same heart rate). The parameters $T_{PQ}$, $T_{ST}$, $D_{PQ}$ and $D_{ST}$ would typically be set with the programmer 68 of FIG. 1 by the patient's doctor at the time the cardiosaver 5 is implanted so as to best match the morphology of the patient's electrogram signal and normal heart rate. $V_{PQ}$ (512), $V_{ST}$ (514), $V_R$ (503) and $\Delta V$ (510) are examples of per-beat heart signal parameters for the beat 500.

Although it may be effective to fix the values of time offsets $T_{PQ}$ (502) and $T_{ST}$ (504) and the durations $D_{PQ}$ (506) and $D_{ST}$ (508), it is envisioned that the time offsets $T_{PQ}$ and $T_{ST}$ and the durations $D_{PQ}$ and $D_{ST}$ could be automatically adjusted by the cardiosaver 5 to account for changes in the patient's heart rate. If the heart rate increases or decreases, as compared with the patient's normal heart rate, it envisioned that the offsets $T_{PQ}$ (502) and $T_{ST}$ (504) and/or the durations $D_{PQ}$ (506) and $D_{ST}$ (508) could vary depending upon the R-R interval between beats or the average R-R interval for an electrogram segment. A simple technique for doing this would vary the offsets $T_N$ and $T_{ST}$ and the durations $D_{PQ}$ and $D_{ST}$ in proportion to the change in R-R interval. For example if the patient's normal heart rate is 60 beats per minute, the R-R interval is 1 second; at 80 beats per minute the R-R interval is 0.75 seconds, a 25% decrease. This could automatically produce a 25% decrease in the values of $T_{PQ}$, $T_{ST}$, $D_{PQ}$ and $D_{ST}$. Alternately, the values for $T_{PQ}$, $T_{ST}$, $D_{PQ}$ and $D_{ST}$ could be fixed for each of up to 20 preset heart rate ranges. In either case, it is envisioned that after the device has been implanted, the patient's physician would, through the programmer 68 of FIG. 1, download from the cardiosaver 5 to the programmer 68, a recent electrogram segment from the recent electrogram memory 472. The physician would then use the programmer 68 to select the values of $T_{PQ}$, $T_{ST}$, $D_{PQ}$ and $D_{ST}$ for the heart rate in the downloaded recent electrogram segment. The programmer 68 would then allow the physician to choose to either manually specify the values of $T_{PQ}$, $T_{ST}$, $D_{PQ}$ and $D_{ST}$ for each heart rate range or have the cardiosaver 5 automatically adjust the values of $T_{PQ}$, $T_{ST}$, $D_{PQ}$ and $D_{ST}$ based on the R-R interval for each beat of any electrogram segment collected in the future by the cardiosaver 5. It is also envisioned that only the offset times, $T_{PQ}$ and $T_{ST}$, might be automatically adjusted and the durations $D_{PQ}$ and $D_{ST}$ would be fixed so that the average values of the ST and PQ segments $V_{PQ}$ (512), $V_{ST}$ (514), $V'_{PQ}$ (512') and $V'_{ST}$ (514') would always use the same number of data samples for averaging.

While the simplest method of adjusting the times $T_{PQ}$ and $T_{ST}$ is to adjust them in proportion to the R-R interval from the preceding R wage to the R wave of the current beat, a preferred embodiment of the present invention is to adjust the times $T_{PQ}$ and $T_{ST}$ in proportion to the square root of the R-R interval from the preceding R wage to the R wave of the current beat.

When used in pacemakers or combination pacemaker/ICDs it envisioned that the start time $T_{ST}$ and duration $D_{ST}$ of the ST segment may have different values than during sinus rhythm (when the pacemaker is not pacing) as pacing the heart changes the characteristics of ischemic ST shifts causing them to occur later relative to the start of the R wave. It is also envisioned, that the offset for the start of the ST segment may be better measured from the S Wave instead of the R wave used for sinus rhythm when the pacemaker is not pacing. The technique of using different timing parameters for start and duration when pacing can be applied to analysis of any sub-segment of the electrogram including the sub-segment that includes the T wave peak.

Various techniques have been used to detect the R and S waves in electrogram data. A well known technique is to look for a change in slope that exceeds a programmed threshold. Because the polarity of the wave depends on electrode placement in surface ECG, the slope threshold is the same for both positive and negative slopes. Because the guardian system has the polarity in a right ventricle to implanted device fixed, the present invention envisions using different threshold values for positive and negative slopes to better detect paced beats and/or PVCs.

An example of a sequence of steps used to calculate the ST deviation 510 for the normal beat 500 are as follows:
1. Identify the time $T_R$ (509) for the peak of the R wave for the beat 500,
2. Calculate the time since the previous R wave and use that time to look up or calculate the values of $T_{PQ}$, $T_{ST}$, $D_{PQ}$ and $D_{ST}$.
3. Average the amplitude of the PQ segment 501 between the times $(T_R-T_{PQ})$ and $(T_R-T_{PQ}+D_{PQ})$ to create the PQ segment average amplitude $V_{PQ}$ (512),
4. Average the amplitude of the ST segment 505 between the times $(T_R+T_{ST})$ and $(T_R+T_{ST}+D_{ST})$ to create the ST segment average amplitude $V_{ST}$ (514),
5. Subtract $V_{PQ}$ (512) from $V_{ST}$ (514) to produce the ST deviation $\Delta V$ (510) for the beat 500.

Although only one normal beat 500 is shown here, there would typically be multiple beats saved in the Y second long electrogram segments stored in the recent electrogram memory 472 and the baseline electrogram memory 474 of FIG. 4. At preset time intervals during the day step 458 of FIG. 5 will run the baseline parameter extraction subroutine 440 that will calculate the "average baseline ST deviation" $\Delta V_{BASE}$ defined as the average of the ST deviations $\Delta V$ (510) for at least two beats of a baseline electrogram segment. Typically the ST deviation of 4 to 8 beats of the baseline electrogram segment will be averaged to produce the average baseline ST deviation $\Delta V_{BASE}$.

For each of "i" preset times during the day (at a time interval of approximately 2 W) an average baseline ST deviation $\Delta V_{BASE}(i)$ will be calculated and saved in the calculated baseline data memory 475 for later comparison with the ST deviation $\Delta V$ (510) of each beat of a recently collected electrogram. For example, in a preferred embodiment of the present invention, the average baseline ST deviation $\Delta V_{BASE}(i)$ is collected once an hour and there are be 24 values of $\Delta V_{BASE}(i)$ ($\Delta V_{BASE}(1)$, $\Box\Delta V_{BASE}(2)$ . . . $\Delta V_{BASE}(24)$) stored in the calculated baseline data memory 475 of FIG. 4. An excessive ST shift for a single beat of a recently collected electrogram segment is then detected when the ST deviation $\Delta V$ for that beat shifts by more than a predetermined threshold amplitude from the average baseline ST deviation $\Delta V_{BASE}(i)$ collected approximately 24 hours before.

The ST shift of a given beat is calculated by subtracting the appropriate averaged baseline ST deviation $\Delta V_{BASE}$ (i) from the ST deviation $\Delta V$ for that beat. Assuming the R-R interval indicates that the heart rate for a beat is in the normal range then an excessive ST shift for a single beat is detected if $(\Delta V - \Delta V_{BASE}$ (i)) is greater than the normal ST shift threshold $H_{normal}$ for the normal heart rate range. The heart signal processing program 450 of FIG. 5 requires that such an excessive ST shift be positively identified in M out of N beats in three successive recent electrogram segments before the alarm subroutine 490 is activated. The threshold $H_{normal}$ may be a fixed value that does not change over time and is set at the time of programming of the cardiosaver 5 with the programmer 68 of FIG. 1.

In a preferred embodiment, the threshold for detection of excessive ST shift is not fixed but is calculated as $H_{ST}(i)$ from the i'th baseline electrogram segment stored in the baseline electrogram memory 474 of FIG. 4. To do this the difference between the amplitude of the peak of the R wave $V_R$ (503) and the average PQ segment amplitude $V_{PQ}$ (512) are calculated for each of at least 2 beats of each baseline electrogram segment by the baseline parameter extraction subroutine 440. The average value $\Delta R(i)$ of this difference $(V_R - V_{PQ})$ for at least two beats of the i'th baseline electrogram segment can be used to produce a threshold for ST shift detection $H_{ST}(i)$ that is proportional to the signal strength of the i'th baseline electrogram segment. The advantage of this technique is that, if the signal strength of the electrogram changes slowly over time, the threshold $H_{ST}(i)$ for ST shift detection will change in proportion.

The preferred embodiment of the present invention would have a preset percentage $P_{ST}$ that is multiplied by $\Delta R(i)$ to obtain the threshold $H_{ST}(i)=P_{ST}\times\Delta R(i)$. Thus, the threshold $H_{ST}(i)$ would be a fixed percentage of the average height of the R wave peaks over the ST segments of the i'th baseline electrogram segment. For example, if $P_{ST}$ is 25% an excessive ST shift on a given beat would be detected if the ST shift $(\Delta V - \Delta V_{BASE}(i))$ is greater than the threshold $H_{ST}(i)$ where $H_{ST}(i)$ is 25% of the average PQ to R height $\Delta R(i)$ of the i'th baseline electrogram segment.

In a preferred embodiment of the present invention heart signal processing program 450 of FIG. 5, the value X and Z are both 20 seconds, Y is 10 seconds, 2 W is 60 minutes, U is 24 hours, W is 30 minutes, M is 6 and N is 8. Therefore the steps 457 and 469 of FIG. 5 will check for excessive ST shifts in 6 out of 8 beats from of the Y=10 second long electrogram segment captured every 30 seconds as compared with parameters extracted from the baseline electrogram segment captured 24±½ hour before. In this preferred embodiment baseline electrogram segments are captured once per hour.

FIG. 7 illustrates a preferred embodiment of the baseline extraction subroutine 440. The subroutine 440 begins in step 439 by saving in the i'th memory location in baseline electrogram memory 474 of FIG. 4, the last Y second long electrogram segment saved into the "Recent" electrogram memory in step 454 of FIG. 5. This Y seconds of electrogram data then becomes the baseline electrogram segment for calculating parameters for detection to be used during the 2 W long period of time U±W minutes in the future.

Next in step 441 the baseline extraction subroutine 440 finds the R wave peak times $T_R(j)$ for the $1^{st}$ through $(N+2)^{th}$ beat (j=1 through N+2) in the baseline electrogram segment saved in step 439. This is a total of N+2 beats. Each time $T_R(j)$ is typically counted from the beginning of the Y second long electrogram segment until the peak of the j'th R wave.

Next in step 442 the average R-R interval of the i'th baseline electrogram segment RR(i) is calculated by averaging the R-R intervals for each of the N+1 beats (j=2 through N+2) where the R-R interval for beat j is $T_R(j)-T_R(j-1)$. For example, for beat 2, the R-R interval is the time interval from the R wave peak of beat 1 (the very first R wave) to the R wave peak of beat 2. I.e. R-R intervals before and after each of the N beats j=2 through j=N+1 are calculated. This step also identifies any R-R intervals that are out of the "normal" range as defined in the programming of the cardiosaver 5. In a preferred embodiment of the present invention, baseline data will only be extracted from "normal" beats. A normal beat is one in which the R-R interval both before and after the R wave is in the "normal" range. This is a preferred technique to use as a too short R-R interval before the R wave can affect the PQ segment amplitude and a too short R-R interval after the R wave can affect the ST segment amplitude, either of which could produce a false indication of excessive ST shift.

Next in step 443 the offsets $T_{PQ}$, $T_{ST}$, $D_{PQ}$ and $D_{ST}$ (see FIG. 6) are calculated. In one embodiment, $T_{PQ}$ and $T_{ST}$ are the percentages $\phi_{PQ}$ and $\phi_{ST}$ multiplied by the average R-R interval RR(i) respectively. This technique will adjust the location of the start of the PQ and ST segments to account for changes in heart rate. The percentages $\phi_{PQ}$ and $\phi_{ST}$ would be selected by the patient's doctor based on "normal" electrogram segments analyzed by the programmer 68 of FIG. 1. Another embodiment of the present invention uses fixed time offsets $T_{PQ}$ and $T_{ST}$ that are programmed by the patient's doctor. Similarly the duration of the PQ and ST segments $D_{PQ}$ and $D_{ST}$ (see FIG. 6) can be calculated by multiplying the percentages $\delta_{PQ}$ and $\delta_{ST}$ times the average R-R interval RR(i) respectively. The percentages $\delta_{PQ}$ and $\delta_{ST}$ would also be selected by the patient's doctor using the programmer 68. The preferred embodiment of the present invention uses fixed segment durations $D_{PQ}$ and $D_{ST}$ that are programmed by the patient's doctor. Using fixed durations $D_{PQ}$ and $D_{ST}$ has the advantage of keeping the same number of samples averaged in each calculation of the average PQ and ST segment amplitudes $V_{PQ}$ and $V_{ST}$ respectively.

Next in step 444 for each of the N beats (j=2 through N+1) identified by step 422 as a normal beat, $V_{PQ}(j)$ the average of the PQ segment amplitude of the j'th beat over the duration $D_{PQ}$ beginning $T_{PQ}$ before the peak $T_R(j)$ and $V_{ST}(j)$ the average ST segment amplitude of the j'th beat over the duration $D_{ST}$ beginning $T_{ST}$ after the time $T_R(j)$ are calculated. Similarly, step 444 calculates the peak T wave heights $V_T(j)$.

For each beat the ST deviation $\Delta V_{ST}(j)$ that is the difference between $V_{ST}(j)$ and $V_{PQ}(j)$ is then calculated in step 445. Similarly, step 445 calculates the T wave deviation $\Delta V_T(j)$ that is the difference between $V_T(j)$ and $V_{PQ}(j)$. It should be noted that step 455 of FIG. 5 will only allow the baseline extraction subroutine to be run if less than 2 too short beats are present, thus at least N−2 of the N beats used for baseline data extraction will be normal beats. Although there is a limit here of less than 2 short beats, it is envisioned that other minimum numbers of short beats than 2 might also be used.

Next in step 446 the ST deviation $\Delta V_{ST}(j)$ for all normal beats within the N beats is averaged to produce the i'th average baseline ST deviation $\Delta V_{BASE}(i)$. Similarly, in step 446 the T wave deviation $\Delta V_T(j)$ for all normal beats within the N beats is averaged to produce the i'th average baseline T wave deviation $\Delta T_{BASE}(i)$.

An alternate embodiment of the present invention would also check for excessive ST shift on each normal beat and exclude any such beats from the average baseline ST deviation and T wave deviation calculations.

Next in step 447, AR(i) the average of the height of the peak of the j'th R wave above the average PQ segment $V_{PQ}(j)$ is calculated for the normal beats. $\Delta R(i)$ acts as an indication of the average signal strength of the i'th baseline electrogram segment. $\Delta R(i)$ is used to provide a detection threshold for excessive ST shift that will adapt to slow changes in electrogram signal strength over time. This is of most value following implant as the sensitivity of the electrodes 14 and 17 may change as the implant site heals.

$\Delta T_{BASE}(i)$ can either be the average of the signal samples of the entire T waves or it can be the average of the peak amplitude of the T waves in the normal beats. It is also envisioned, that if both ST and T wave shift detection are used, a cardiac event could be declared if either excessive ST shift or T wave shift detects a change (this is preferred) or the program could require that both excessive ST shift and T wave shift be present.

Next in step 448, the threshold for ST shift detection for normal heart rates $H_{ST}(i)$ is calculated by multiplying the programmed threshold percentage $P_{ST}$ of $\Delta R(i)$. Also in step 448, if the T wave shift detector is being used, the threshold for T wave shift detection for normal heart rates $H_T(i)$ is calculated by multiplying the programmed threshold percentage $P_T$ of $\Delta R(i)$.

Finally in step 449, the extracted baseline parameters $\Delta V_{BASE}(i)$, $\Delta T_{BASE}(i)$, $\Delta R(i)$, $H_{ST}(i)$ and $H_T(i)$ are saved to the calculated baseline data memory 475. The baseline extraction subroutine 440 has ended and the program returns to the main heart signal processing program 450 step 451 of FIG. 5.

One embodiment of ST shift and T wave shift detection might use a baseline for ST shift detection that is 24±½ hour before and a baseline for T wave shift that is 1 to 4 minutes in the past. This would require that the baseline extraction subroutine 440 be run for T wave shift parameters approximately every 60 seconds and for ST segment parameters every hour.

Although the baseline extraction subroutine 440 is described here as using the same "N" as the number of beats processed as the ST shift detection steps 457 and 469 of FIG. 5, it is envisioned that either a greater or lesser number of beats could be used for baseline extraction as compared with the number of beats "N" checked for excessive ST shifts in FIG. 5.

Typical values used for the baseline extraction subroutine 440 as shown in FIG. 7 would be N=8 to average the data over 8 beats using beats 2 through 9 of the Y second long electrogram segment. However, it is envisioned that as few as 1 beat or as many as 100 beats or higher could be used to calculate the parameters extracted by subroutine 440. Also even though the preferred embodiment of the present invention extracts baseline data only from "normal" beats, it is envisioned that using all 8 beats would usually yield an acceptable result.

Although the baseline extraction subroutine 440 shows the extraction of parameters for identifying excessive ST shifts and T wave shifts, the cardiosaver 5 would function with either of these detection methods or could use other techniques to measure the changes in electrogram signals indicating one or more coronary event.

FIG. 8 illustrates a preferred embodiment of the alarm subroutine 490. The alarm subroutine 490 is run when there have been a sufficient number of events detected to warrant a major event cardiac alarm to the patient. The alarm subroutine 490 begins with step 491 where the entire contents of both baseline electrogram memory 474 and recent electrogram memory 472 of FIG. 4 are saved into the event memory 476. This saves the above mentioned electrogram data in a place where it is not overwritten by new baseline or recent electrogram data to allow the patient's physician to review the electrogram segments collected during a period of time that occurred before the alarm. In a preferred embodiment with 24 baseline electrogram segments collected once per hour, and 8 recent electrogram segments collected every 30 seconds, the physician will be able to review a significant amount of electrogram data from the 4 minutes just before the cardiac event as well as being able to see any changes in the 24 hours before the event.

Next; in step 492 the internal alarm signal is turned on by having the CPU 44 of FIG. 4 cause the alarm sub-system 48 to activate a major event alarm signal.

Next in step 493 the alarm subroutine instructs the CPU 44 to send a major event alarm message to the external alarm system 60 of FIG. 1 through the telemetry sub-system 46 and antenna 35 of the cardiosaver 5 of FIG. 4. The alarm message is sent once every L1 seconds for L2 minutes. During this time step 494 waits for an acknowledgement that the external alarm has received the alarm message. After L2 minutes, if no acknowledgement is received, the cardiosaver 5 of FIG. 1 gives up trying to contact the external alarm system 60. If an acknowledgement is received before L2 minutes, step 495 transmits alarm related data to the external alarm system. This alarm related data would typically include the cause of the alarm, baseline and last event electrogram segments and the time at which the cardiac event was detected.

Next in step 496, the cardiosaver 5 transmits to the external alarm system 60 of FIG. 1 other data selected by the patient's physician using the programmer 69 during programming of the cardiosaver. These data may include the detection thresholds $H_{ST}(i)$, $H_T(i)$ and other parameters and electrogram segments stored in the cardiosaver memory 47.

Once the internal alarm signal has been activated by step 492, it will stay on until the clock/timing sub-system 49 of FIG. 4 indicates that a preset time interval of L3 minutes has elapsed or the cardiosaver 5 receives a signal from the external alarm system 60 of FIG. 1 requesting the alarm be turned off.

To save power in the implantable cardiosaver 5, step 496 might check once every minute for the turn off signal from the external alarm system 60 while the external alarm system 60 would transmit the signal continuously for slightly more than a minute so that it will not be missed. It is also envisioned that when the alarm is sent to the external alarm system 60, the internal clock 49 of the cardiosaver 5 and the external alarm system 60 can be synchronized so that the programming in the external alarm system 60 will know when to the second, that the cardiosaver will be looking for the turn off signal.

At this point in the alarm subroutine 490 step 497 begins to record and save to event memory 476 of FIG. 4, an E second long electrogram segment every F seconds for G hours, to allow the patient's physician and/or emergency room medical professional to read out the patient's electrogram over time following the events that triggered the alarm. This is of particular significance if the patient, his caregiver or paramedic injects a thrombolytic or anti-platelet drug to attempt to relieve the blood clot causing the acute myocardial infarction. By examining the data following the injection, the effect on the patient can be noted and appropriate further treatment prescribed.

In step 498 the alarm subroutine will then wait until a reset signal is received from the physician's programmer 68 or the patient operated initiator 55 of the external alarm system 60 of FIG. 1. The reset signal would typically be given after the event memory 476 of FIG. 4 has been transferred to a component of the external equipment 7 of FIG. 1. The reset signal will clear the event memory 476 (step 499) and restart the main program 450 at step 451.

If no reset signal is received in L6 hours, then the alarm subroutine 490 returns to step 451 of FIG. 5 and the cardiosaver 5 will once again begin processing electrogram segments to detect a cardiac event. If another event is then detected, the section of event memory 476 used for saving post-event electrogram data would be overwritten with the pre-event electrogram data from the new event. This process will continue until all event memory is used. I.e. it is more important to see the electrogram data leading up to an event than the data following detection.

Figure 9:
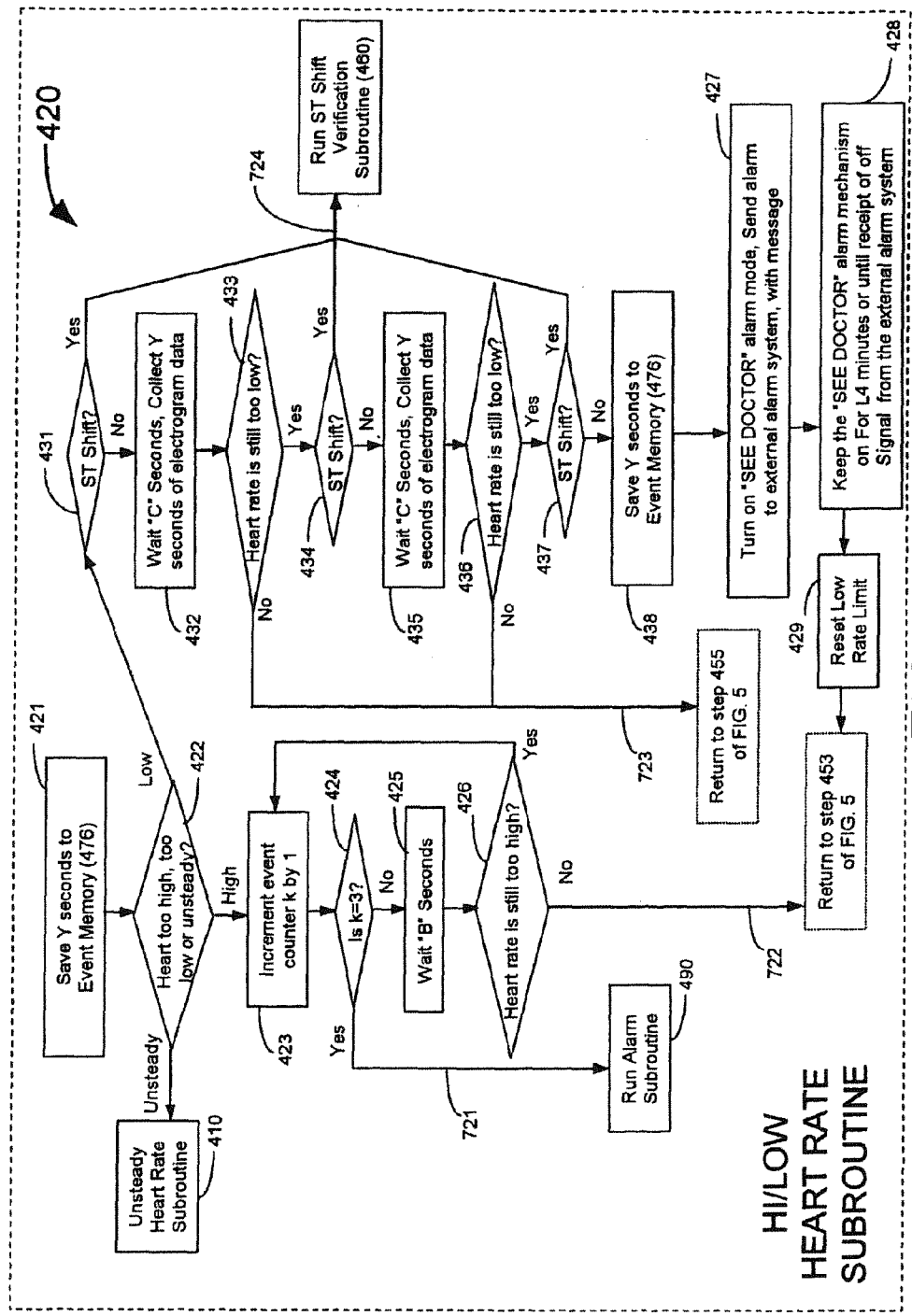
FIG. 9 is a block diagram of the hi/low heart rate subroutine of the cardiosaver event detection program.

FIG. 9 illustrates the function of the hi/low heart rate subroutine 420. The hi/low heart rate subroutine is meant to run when the patient's heart rate is below the normal range (e.g. 50 to 80 beats per minute) or above the elevated range that can occur during exercise (e.g. 80 to 140 beats per minute). A low heart rate (bradycardia) may indicate the need for a pacemaker and should prompt a "SEE DOCTOR" warning to the patient if it does not go away after a programmed period of time. Very high heart rate can be indicative of tachycardia or ventricular fibrillation and is serious if it does not quickly go away and should warrant a major event alarm like a detected AMI.

The hi/low heart rate subroutine 420 begins with step 421 where the electrogram segment of Y seconds collected in steps 453 and 454 of FIG. 5 is saved to the event memory 476 (step 421) because the patient's doctor may wish to know that the high or low heart rate occurred. Once the Y second long electrogram segment is saved, step 422 of the hi/low heart rate subroutine 420 directs the processing in different directions depending on if the heart rate is too high, too low or unsteady. If unsteady, the unsteady heart rate subroutine 410 illustrated in FIG. 12 is run. If it is too high, step 423 increments the event counter k by 1, then step 424 checks whether the event counter k is equal to 3. Although this embodiment uses k=3 events as the trigger to run the alarm subroutine 490 it is envisioned that k=1 or 2 or k values higher than 3 can also be used.

In step 424, If k=3 then the alarm subroutine 490 illustrated in FIG. 8 is run. If k less than 3 then in step 425 the hi/low heart rate subroutine 420 waits for "B" seconds and checks again in step 426 if the heart rate is still too high. If the heart rate is still too high, the hi/low heart rate subroutine 420 returns to step 423 where the event counter is incremented by 1. If the heart rate remains high, the hi/low heart rate subroutine 420 will loop until k is equal to 3 and the alarm subroutine 490 is run. If the heart rate does not remain high in step 426, the hi/low heart rate subroutine 420 will return to step 453 of the main heart signal processing program 450 illustrated in FIG. 5. ST shift amplitude (and/or T wave shift) is not checked during the high heart rate section of the hi/low heart rate subroutine 420 as the presence of a very high heart rate could alter the detection of changes in ST and PQ segments of the electrogram giving false indications. Very high heart rate is, by itself, extremely dangerous to the patient and is therefore a major cardiac event.

If in step 422, the heart rate is too low rather than too high, the hi/low heart rate subroutine 420 will proceed to step 431 where the Y second long electrogram segment is checked for an excessive ST shift in the same way as step 457 of the main heart signal processing program 450 illustrated in FIG. 5. In other words, the ST deviation on M out of N beats must be shifted at least $H_{ST}(i)$ from the baseline average ST deviation $\Delta V_{BASE}(i)$ of the i'th baseline electrogram segment. If there is a detected excessive ST shift in step 431, the hi/low heart rate subroutine 420 returns to run the ST shift verification subroutine 460 illustrated in FIG. 5. As with step 457 of the main heart signal processing program 450, the detection of M−N+1 OK beats without excessive ST shift is sufficient for a negative detection and the program can then proceed on to step 432.

If there is not an excessive ST shift detected in step 431, step 432 causes the hi/low heart rate subroutine 420 in step 432 to wait for "C" seconds then buffer and save a new Y second long electrogram segment as in steps 453 and 454 of the main heart signal processing program 450 of FIG. 5. Once the new Y second long electrogram segment is collected, the hi/low heart rate subroutine 420 checks in step 433 if the heart rate is still too low. If it is no longer too low, the system returns to step 455 of the main heart signal processing program 450 illustrated in FIG. 5. If the heart rate remains too low, then step 434 checks for an excessive ST shift as in step 431. If there is an excessive ST shift in step 434, the hi/low heart rate subroutine 420 returns to run the ST shift verification subroutine 460 of FIG. 5. If there is not an excessive ST shift detected in step 434, step 435 causes the hi/low heart rate subroutine 420 in step 435 to wait for another "C" seconds then buffer and save another Y second long electrogram segment as in steps 453 and 454 of the main heart signal processing program 450 of FIG. 5. Once this Y second long electrogram segment is collected, the hi/low heart rate subroutine 420 checks in step 436 if the heart rate is still too low (for the $3^{rd}$ time). If it is no longer too low, the system returns to step 455 of the main heart signal processing program 450 of FIG. 5. If the heart rate remains too low, then step 437 checks for an excessive ST shift as in steps 431 and 434. If there is an excessive ST shift in step 437, the hi/low heart rate subroutine 420 returns to run the ST shift verification subroutine 460 of FIG. 5. If there is not an excessive ST shift detected in step 437, the step 438 saves the contents of the most recently collected Y second long electrogram segment and the to the event memory 476 for later review by the patient's doctor.

If the hi/low heart rate subroutine 420 reaches step 438 then the patient's heart rate has been too low even after two waits of "C" seconds. Now the hi/low heart rate subroutine 420 proceeds to step 427 to turn on the internal "SEE DOCTOR" alarm signal. Step 427 also sends out to the external alarm system 60 of FIG. 1, a signal to activate the "SEE DOCTOR" alarm signal of the external alarm system 60 that may include a text or played speech message indicating the cause of the alarm. E.G. the external alarm system speaker 57 of FIG. 1 could emit warning tones and a text message could be displayed or the speaker 57 might emit a spoken warning message to the patient.

Note that during the checking for continued low heart rate, ST shift amplitudes are still checked after each wait because it is well known that low heart rate can be a byproduct of an acute myocardial infarction.

Finally in step 428, the hi/low heart rate subroutine 420 will keep the "SEE DOCTOR" alarm signal turned on for L4 minutes or until receipt of a signal from the external alarm system 60 to turn off the alarm signal. After the "SEE DOCTOR alarm signal is enabled, the low heart rate limit, below which the hi/low heart rate subroutine 420 is run, is changed by step 429 to be just below the average heart rate measured in step 436. Once the patient is warned to go see the doctor, additional warnings will be annoying and therefore the low rate limit is best changed. This allows the hi/low heart rate subroutine 420 to then return to step 452 of the main program where it will continue to monitor ST shift amplitudes to provide early detection of acute myocardial infarction. Actual programming of the cardiosaver 5 may use R-R interval instead of heart rate and it is understood that either is sufficient and one can be easily computed from the other.

Although steps 431, 434 and 437 indicate the subroutine 420 is to look for an ST shift, other ischemia indications such as T wave spiking, either alone or in combination with ST shift detection may be used. Also in steps 431, 434 and 437 if no shift is detected, the event counter k is reset to 0 if it is not already 0.

FIG. 10 illustrates the ischemia subroutine 480 that provides decision making for the cardiosaver 5 in the event of an elevated heart rate such as that would occur during exercise by the patient. The ischemia subroutine 480 uses a beat counter j to indicate the beat within a Y second long electrogram segment. A beat is defined as a sub-segment containing exactly one R wave of the Y second long electrogram segment. The ischemia subroutine 480 begins in step 481 by initializing the beat counter j to a value of 2. Then in step 482, the R-R interval range A for the beat j is determined. For example that there could be between 4 R-R interval ranges A=1 to 4 of 750 to 670, 670 to 600, 600 to 500 and 500 to 430 milliseconds respectively. These would correspond to heart rate intervals of 80 to 90, 90 to 100, 100 to 120 and 120 to 140 beats per minute. The number of ranges A and the upper and lower limit of each range would be programmable by the patient's physician from the programmer 68 of FIG. 1.

Next in step 483 the programmed ischemia multiplier μ(A) is retrieved from the programmable parameters 471 of FIG. 4. μ(A) is the allowable factor increase or decrease in ST shift detection threshold for the R-R interval range A. In other words, because the patient may have some ischemia during elevated heart rates from exercise, the patient's physician can program μ(A)s that are greater than 1 and might increase with each successive heart rate range. For example, if the R-R interval ranges are 750 to 670, 670 to 600, 600 to 500 and 500 to 430 milliseconds the corresponding μ(A)s might be 1.1, 1.2, 1.3 and 1.5. This would require that the ST shift in the R-R interval range of A=4 (500 to 430 milliseconds) be one and a half times as large as during normal heart rates in order to qualify as a cardiac event. It is envisioned that the patient could undergo an exercise stress test at a time after implant when the implanted leads have healed into the wall of the heart and electrogram segments captured by the cardiosaver 5 during that stress test would be reviewed by the patient's physician to determine the appropriate range intervals and ischemia multipliers to help identify a worsening of the patient's exercise induced ischemia from the time when the stress test is conducted.

It is also envisioned that in order to detect smaller changes in vessel narrowing than a full acute myocardial infarction, the cardiosaver 5 of FIGS. 1-4 might use μ(A)s that are less than one. For example, if the R-R interval ranges are 750 to 670, 670 to 600, 600 to 500 and 500 to 430 milliseconds the corresponding μ(A)s might be 0.5, 0.6, 0.7 and 0.8. Thus in this example, in the R-R interval range of 750 to 670 milliseconds, the threshold for ischemia detection would be half of what it is for the normal heart rate range.

Once the ischemia multiplier has been retrieved, step 484 calculates the ischemia ST shift threshold θ(A) for the R-R interval range A where θ(A)=$H_{ST}(i) \times \mu(A)$ where $H_{ST}(i)$ is the current ST shift threshold for normal heart rates. Next in step 485, the ischemia subroutine 480 checks if for the beat j the ST shift is greater than the ischemia threshold θ(A). If it is not greater, step 487 then checks if the N'th beat has been examined. If the ST shift of the j'th beat exceeds the ischemia threshold θ(A) then step 486 checks if M beats with ST shifts greater than θ(A) have been seen. If they have not been seen proceed to step 487. If in step 487, the Nth beat has been examined, return to step 451 of the main heart signal processing program 450 of FIG. 5. If N beats have not yet been examined, increment j by 1 in step 489 and loop back to step 482.

If M beats with excessive ST shift are found by step 486, step 581 saves the current Y second long electrogram segment to the Event Memory 476, then in step 582 the event counter k is incremented by 1 followed by step 583 checking if k is equal to 3. If k is less than 3 then the ischemia subroutine 480 continues by sleeping for Z seconds in step 584, then buffering a new Y second long electrogram segment in step 585, saving in step 586 the new Y second long electrogram segment to the next location in recent electrogram memory 472 of FIG. 4. and then checking if the heart rate is still elevated in step 587. If the heart rate is still elevated in step 587, the loop checking for ischemia is run again starting with step 481. If the heart rate is no longer elevated then step 588 checks if the heart rate is too high, too low or unsteady. If such is the case, the hi/low heart rate subroutine 420 is run. If the heart rate is not high, low or unsteady, the ischemia subroutine 480 ends and the program returns to step 469 of the ST shift verification subroutine 460 of FIG. 5. This will allow an excessive ST shift detected at elevated heart rate that stays shifted when the heart rate returns to normal to quickly trigger the AMI alarm. This works because k is either 1 or 2 at this point so either 2 or 1 more detection of excessive ST shift with normal heart rate will cause a major event AMI alarm. If however k=3 in step 582, then the last detection of excessive ST shift occurred during an elevated heart rate and will be treated as exercise induced ischemia rather than an acute myocardial infarction.

So if k=3 (i.e. exercise induced ischemia has been detected) in step 582 the ischemia subroutine 480 moves on to step 681 where it checks if it has been more than L5 minutes since the first time that exercise induced ischemia was detected where k=3 in step 583.

If it has been less than L5 minutes since the first detection of exercise induced ischemia then the internal SEE DOCTOR alarm signal is turned on by step 682 if it has not already been activated.

If it has been more than L5 minutes, then the alarm subroutine 490 is run. This will change the SEE DOCTOR alarm signal previously started in step 682 to a major event AMI alarm if the excessive ST shift at an elevated heart rate does not go away within L5 minutes. Similarly, if the patient stops exercising and his heart rate returns to normal but the excessive ST shift remains, then the alarm subroutine 490 will also be run.

If it has been less than L5 minutes and the SEE DOCTOR alarm signal has not been already been activated, step 683 next sends a message to the external alarm system 60 of FIG. 1 to activate the SEE DOCTOR external alarm signal and indicate to the patient by a text of spoken message that he should stop whatever he is doing, and sit or lie down to get his heart rate to return to normal. Following this, in step 684 the ischemia subroutine 480 will keep the SEE DOCTOR alarm signal on for L4 minutes from the first time it is turned on or until the receipt of an off signal from the alarm disable button 59 of the external alarm system 60 of FIG. 1. The program then returns to step 451 of the main program 451 of FIG. 5 to continue to examine the patient's heart signals.

FIG. 11 diagrams the alarm conditions 600 that are examples of the combinations of major and minor events that can trigger an internal alarm signal (and/or external alarm signal for the guardian system of FIG. 1. Box 610 shows the combinations 611 through 617 of major cardiac events that can cause the alarm subroutine 490 to be run. These include the following:

611. 3 ST shift events (detections of excessive ST shift) with either a normal heart rate or a low heart rate.
612. 2 ST shift events with a normal or low heart rate and 1 event from heart rate too high.
613. 1 ST shift event with a normal or low heart rate and 2 events from heart rate too high.
614. 3 events from heart rate too high.
615. 3 ST shift events with either a normal, low or elevated heart rate (ischemia) where the last detection is at a normal or low heart rate.
616. 3 events (excessive ST shift or high heart rate) where the last event is high heart rate.
617. An ischemia alarm indication from conditions in box 620 that remains for more than L5 minutes after the first detection of ischemia.

The ischemia alarm conditions 620 include:

621. 3 ST shift events with either a normal, low or elevated heart rate (ischemia) where the last detection is at an elevated heart rate.

622. Any 3 events including a too high heart rate event where the last detection is an excessive ST shift at an elevated heart rate.

If either of the ischemia alarm conditions 620 is met and it is less than L5 minutes since the exercise induced ischemia was first detected, then the SEE DOCTOR alarm signal will be turned on by step 682 of the ischemia subroutine 480 if it has not already been activated.

Box 630 shows the other minor event alarm conditions including the bradycardia alarm condition 632 that is three successive electrogram segments collected with heart rate too low and the unsteady heart rate alarm condition 635 that is caused by more than $P_{unsteady}$% of beats having a too short R-R interval. If here are too many (as programmed by the doctor) consecutive electrogram segments with insufficient normal beats 637 to be able to process for cardiac event detection, the programming may need modification or there is something else wrong. These will trigger the SEE DOCTOR alarm signal initiated by step 427 of the hi/low heart rate subroutine 420 for the bradycardia alarm condition 632 and step 416 of the unsteady hart rate subroutine 410 for the unsteady heart rate alarm condition 635. Also triggering the SEE DOCTOR alarm signal is a low battery condition 636.

FIG. 12 is a block diagram illustrating the unsteady heart rate subroutine 410. The subroutine 410 is run if the R-R interval varies greatly over many of the beats in the Y second long electrogram segment collected by steps 453 and 454 of the main heart signal processing program 450. As previously described, one technique for identifying such an unsteady heart rate is to compare the two shortest R-R intervals and the 2 longest intervals. If the difference between the both of the two shortest and the average of the two longest R-R intervals are more than a programmed percentage $\alpha$, an unsteady heart rate is identified. For example the programmed percentage $\alpha$ □ might be 25% so that if the two shortest R-R intervals are each more than 25% less than the average of the two longest R-R intervals, then the heart rate is unsteady. It is envisioned that if a longer time Y is used for electrogram segment collection then it might require 3 or more "short" beats to indicated an unsteady heart rate. If there is zero or one short beat, the main heart signal processing program 450 will move on to step 456 having marked all of the "normal" beats in the Y second long electrogram segment. A normal beat is defined as a beat including where the R-R intervals before and after the R wave are both in the normal range (i.e. not too short).

The unsteady heart rate subroutine 410 begins in step 411 by checking for at least N normal beats in the most recently collected electrogram data. When the subroutine begins there is only one Y second long electrogram segment being examined. If there are not N normal beats, then the subroutine 410 will wait X seconds in step 419 before an additional Y second long electrogram segment is collected in step 412 after the . Step 411 then will check for N normal beats in the two Y second long electrogram segments (i.e. 2 Y seconds of electrogram data). This loop of steps 411 and 412, where each time Y additional seconds of electrogram is collected, will continue until N normal beats are found.

It is envisioned that step 411 could also check for beats with elevated heart rate R-R intervals or might include elevated heart rate beats as "normal" beats by expanding the allowed range of the R-R interval for a normal beat. Once N "normal" beats are found by step 411, then step 413 checks for an excessive ST shift in M out of the N normal beats similar to step 457 of FIG. 5. Step 413 could also (as in step 457 of FIG. 5) look for an excessive T wave shift. If an excessive ST shift (and/or T wave shift) is detected by step 413, the program returns to the ST shift verification subroutine 460 of FIG. 5.

If excessive ST shift (and/or T wave shift) are not detected by step 413, then step 414A checks if more than $P_{unsteady}$% of all the beats (not just the normal beats) in the electrogram data collected have a too short R-R interval as defined above by the programmed parameter $\alpha$. If not the program returns to step 451 of the main heart signal processing program 450 of FIG. 5. If, however, more than $P_{unsteady}$% of the beats have a short R-R interval, then step 414B ascertains if there have been $N_u$ sequential electrogram segments having more than $P_{unsteady}$% of the beats with short R-R intervals. If the number is less than $N_u$ then this then the program returns to step 451 of the main heart signal processing program 450 of FIG. 5. If the number is $N_u$ then step 415 saves all the current electrogram data to event memory 476 of FIG. 4 and step 416 turns on the SEE DOCTOR alarm signal with the internal alarm sub-system 48 of FIG. 4 and also initiates an external alarm signal by the external alarm system 60 of FIG. 1 with a text or spoken message to the patient indicating that the SEE DOCTOR alarm signal is the result of detection of unsteady heart rate. As in the case of other SEE DOCTOR alarm signals, step 417 will keep the "See Doctor" alarm mechanism turned on for L4 minutes from the first detection of unsteady heart rate or until receipt of a signal from the external alarm system 60 to turn off the alarm.

To avoid continuously alarming the patient, once the SEE DOCTOR alarm has sounded, the system will wait for a preset time programmed by the patient's physician before allowing reactivation of the SEE DOCTOR ALARM. Alternately, there may be a default wait period such as 12 hours or 1 day or the system may be programmed to only sound the SEE DOCTOR alarm once for each indication until reset by the physician's programmer.

Figure 13:
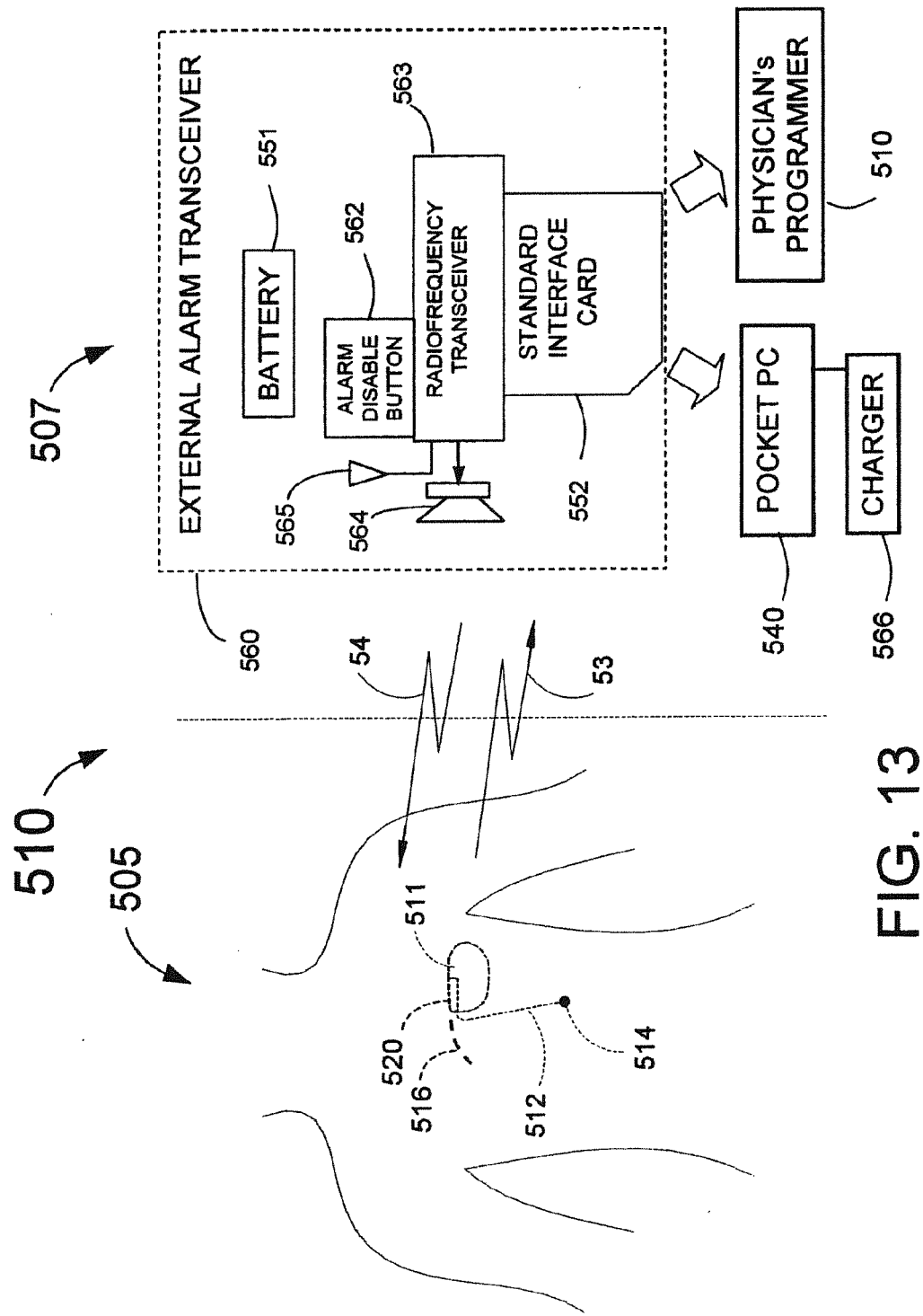
FIG. 13 is an alternate embodiment of the guardian system.

FIG. 13 shows a modified embodiment of the guardian system 510. The cardiosaver implant 505 with lead 512, electrode 514, antenna 516, header 520 and metal case 511 would be implanted subcutaneously in a patient at risk of having a serious cardiac event such as an acute myocardial infarction. The lead 512 could be placed either subcutaneously or into the patient's heart. The case 511 would act as the indifferent electrode. The system 510 also included external equipment that includes a physician's programmer 510 an external alarm transceiver 560 and a pocket PC 540 with charger 566. The external alarm transceiver 560 has its own battery 561 and includes an alarm disable button 562 radiofrequency transceiver 563, speaker 564, antenna 565 and standard interface card 552. The cardiosaver 505 has the same capabilities as the cardiosaver 5 of FIGS. 1 through 4.

The standardized interface card 552 of the external alarm transceiver 510 can be inserted into a standardized interface card slot in a handheld or laptop computer. The pocket PC 540 is such a handheld computer. The physician's programmer 510 is typically a laptop computer. Such standardized card slots include compact flash card slots, PCMCIA adapter (PC adapter) card slots, memory stick card slots, Secure Digital (SD) card slots and Multi-Media card slots. The external alarm transceiver 510 is designed to operate by itself as a self-contained external alarm system, however when inserted into the standardized card slot in the pocket PC 540, the combination forms an external alarm system with enhanced functionality. For example, in stand alone mode without the pocket PC 540, the external alarm transceiver 560 can receive alarm notifications from the cardiosaver implant 505 and can produce an external alarm signal by generating one or more sounds through the speaker 564. These sounds can wake the patient up or provide additional alerting to that provided by the internal alarm signal generated by the cardiosaver 505. The alarm disable button 562 can acknowledge and turn off both external and internal alarm signals. The standalone external alarm transceiver 560 therefore provides key functionality could be small enough to wear on a chain around the neck or on a belt.

When plugged into the pocket PC 540, the external alarm transceiver 560 can facilitate the display of text messages to the patient and electrogram data that is transmitted from the cardiosaver 505. The pocket PC 540 also enables the patient operated initiator 55 and panic button 52 capabilities of the external alarm system 60 of FIG. 1. Being a pocket PC also readily allows connection to wireless communication capabilities such as wireless internet access that will facilitate retransmission of data to a medical practitioner at a geographically remote location. It is also envisioned that the charger 566 could recharge the batter 551 when the external alarm adaptor 560 is plugged into the pocket PC 540.

The external alarm transceiver 560 can also serve as the wireless two-way communications interface between the cardiosaver 505 and the programmer 510. The physician's programmer 510 is typically a laptop computer running some version of the Microsoft Windows operating system. As such, any or the above standardized slot interfaces can be either directly interfaced to such a laptop computer or interfaced using a readily available conversion adaptor. For example, almost all laptop computers have a PCMCIA slot and PCMCIA card adaptors are available for compact flash cards, Secure Digital cards etc. Thus the external alarm adaptor 560 could provide the interface to the physician's programmer 510. This provides additional security as each cardiosaver implant 505 and external alarm adaptor 560 could be uniquely paired with built in security codes so that to program the implant 505, the physician would need the patient's external alarm adaptor 560 that would act both as a wireless transceiver and as a security key.

Although the guardian system 10 as described herein could clearly operate as a stand-alone system, it is clearly conceivable to utilize the guardian system 10 with additional pacemaker or implanted defibrillator circuitry. As shown in FIG. 4, pacemaker circuitry 170 and/or defibrillator circuitry 180 could be made part of any cardiosaver 5 or 505. Furthermore, two separate devices (one pacemaker or one defibrillator plus one cardiosaver 5) could be implanted within the same patient.

FIG. 14 illustrates a preferred physical embodiment of the external alarm transceiver 560 having standardized interface card 552, alarm disable button 562 labeled "ALARM OFF" and speaker 564. It is also envisioned that by depressing and holding the alarm disable button 562 for a minimum length of time, when there is not an alarm, the external alarm transceiver could verify the operational status of the cardiosaver 505 and emit a confirming sound from the speaker 564.

FIG. 15 illustrates the physical embodiment of the combined external alarm transceiver 560 and pocket PC 540 where the standardized interface card 552 has been inserted into a matching standardized interface card slot the pocket PC 540. The screen 542 of the pocket PC 540 shows an example of the display produced by an external alarm system following the detection of an acute myocardial infarction by the cardiosaver 505. The screen 542 of FIG. 15 displays the time of the alarm, the recent electrogram segment from which the cardiac event was detected and the baseline electrogram segment used for comparison in the cardiac event detection. Such a display would greatly facilitate diagnosis of the patient's condition upon arrival at an emergency room and could eliminate the need for additional electrocardiogram measurements before the patient is treated.

Figure 16:
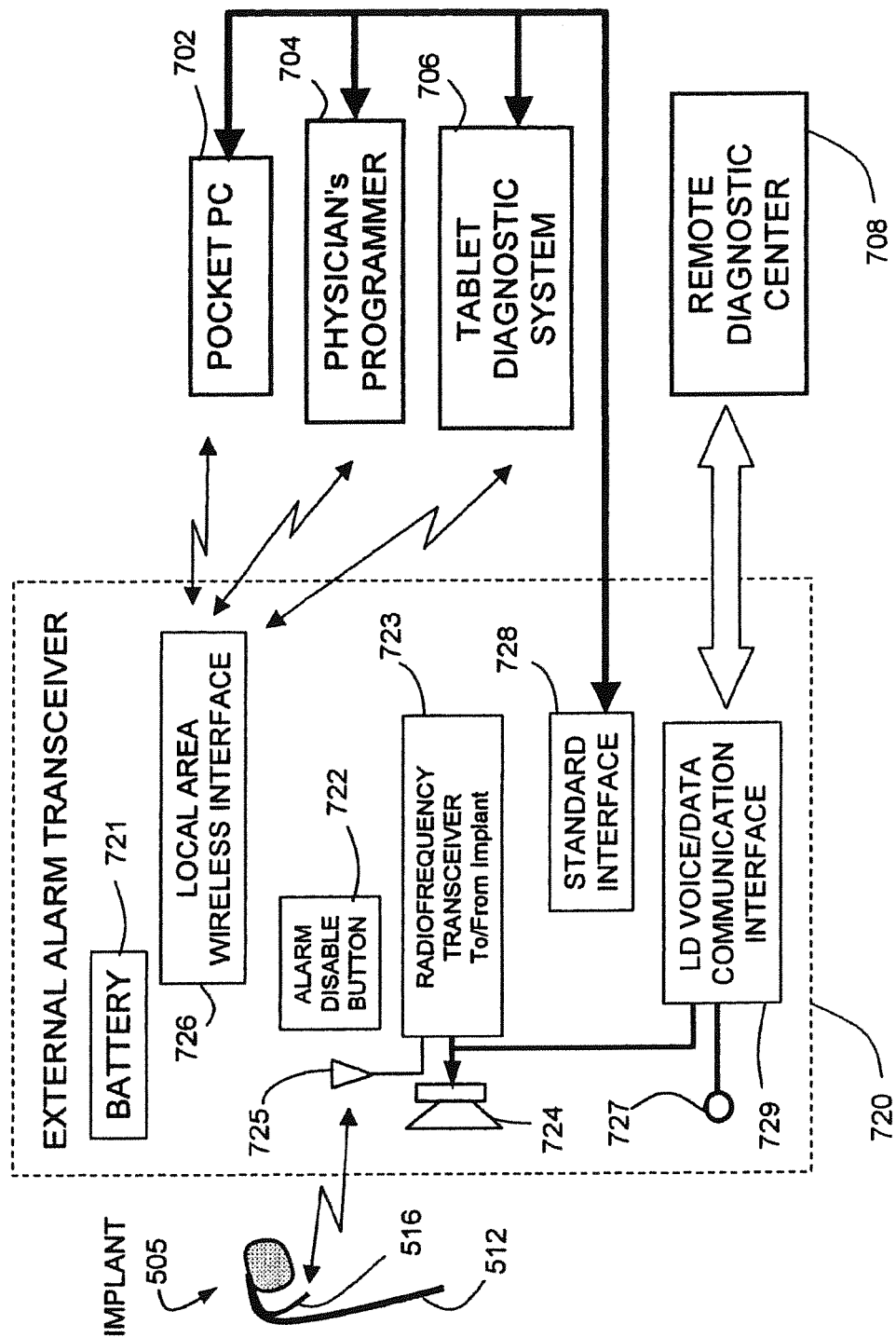
FIG. 16 is another alternate embodiment of the guardian system.

FIG. 16 shows and advanced embodiment of the external alarm transceiver 720 having a battery 721, an alarm disable button 722, a RF transceiver for data communication to and from the implanted device, a loudspeaker 724, a microphone 727, a local area wireless interface 723, a standard interface 728 and a long distance (LD) voice/data communication interface 729. The function of the alarm disable button 722 and the radiofrequency transceiver 723 are as described for the similar devices shown in FIG. 13.

The local area wireless interface 723 provides wireless communication within a building (e.g. home, doctor's office or hospital) to and from the implant 505 with lead 512 and antenna 516 through the external alarm transceiver 720 from and to assorted external equipment such as Pocket PCs 702, Palm OS PDAs, Notebook PCs, physician's programmers 704 and tablet diagnostic systems 706. The means for transmission from the local area wireless interface 723 may be by radiofrequency or infra-red transmission. A preferred embodiment of the local area wireless interface 723 would use a standardized protocol such as IRDA with infra-red transmission and Bluetooth or WiFi (802.11.a, b, or g) with radiofrequency transmission. The local area wireless interface 723 would allow display of implant data and the sending of commands to the implant 505.

The standard interface 728 provides a physical (wired) connection for data communication with devices nearby to the patient for the purposes of displaying data captured by the implant 505 and for sending commands and programs to the implant 505. The standard interface 728 could be any standard computer interface; for example: USB, RS-232 or parallel data interfaces. The pocket PC 702 and physician's programmer 704 would have functionality similar to the pocket PC 540 and physician's programmer 510 of FIG. 13.

The tablet diagnostic system 706 would provide a level of functionality between that of the pocket PC 702 and physician's programmer 706. For example, the tablet diagnostic system would have the programmer's ability to download complete data sets from the implant 505 while the pocket PC is limited to alarm and baseline electrogram segments or the most recent electrogram segment. The tablet diagnostic system 706 would be ideal for an emergency room to allow emergency room medical professionals to quickly view the electrogram data stored within the implant 505 to assess the patient's condition. The recently introduced Tablet PCs such as the Toshiba Portege 3500 or the Compaq TC1000 have IRDA, WiFi and USB interfaces built into them and so would make an ideal platform for the tablet diagnostic system 706. It is envisioned that such a tablet diagnostic system in an emergency room or medical clinic would preferably be connected to its own external alarm transceiver. The tablet diagnostic system 706 could be hand held or mounted on a wall or patient bed. A unit located near the bed of an incoming patient having a guardian implant 505 would enable display of patient diagnostic data without requiring any attachments to the patient. Such wireless diagnosis is similar to that envisioned for the tricorder and diagnostic beds of the Star Trek science fiction series created by Gene Roddenberry.

The long distance voice/data communication interface 729 with microphone 727 and also attached to the loudspeaker 724 will provide the patient with emergency contact with a remote diagnostic center 708. Such a system could work much like the ONSTAR emergency assistance system now built into may cars. For example, when a major alarm is identified by the guardian implant 505, the following steps could be followed:

1. The guardian will first ascertain if an external alarm transceiver is within range, if not the internal alarm will be initiated.
2. If the external alarm transceiver is within range the system will next see if there is access to the remote diagnostic center 708 through the long distance voice/data communication interface 729. If not the external alarm transceiver 720 and implant 505 will initiate internal and/or external alarm notification of the patient.
3. If there is access to the remote diagnostic center 708 the long distance voice/data communication interface 729, the patient alarm information including alarm and baseline electrogram segments will be transmitted to the remote diagnostic center 708. A medical professional at the remote diagnostic center 708 will view the data and immediately establish voice communication to the external alarm transceiver 720 through the long distance voice/data communication interface 729. If this occurs, the first thing that the patient will hear is a ringing tone and/or a voice announcement followed by the contact with the medical professional who can address the patient by name and facilitate appropriate emergency care for the patient. In this case, the internal and external alarms will not be needed and to the patient it will resemble an incoming telephone call from the medical professional. It is also envisioned that the voice of the medical professional could be the first thing that the patient hears although an initial alerting signal is preferred.

This method of establishing the highest level of communication available to the guardian system with the fall back of just the internal alarm will provide the best possible patient alerting based on what is available at the time of the alarm.

Although throughout this specification all patients have been referred to in the masculine gender, it is of course understood that patients could be male or female. Furthermore, although the only electrogram indications for an acute myocardial infarction that are discussed herein are shifts involving the ST segment and T wave height, it should be understood that other changes in the electrogram (depending on where in the heart the occlusion has occurred and where the electrodes are placed) could also be used to determine that an acute myocardial infarction is occurring. Furthermore, sensors such as heart motion sensors, or devices to measure pressure, $pO_2$ or any other indication of an acute myocardial infarction or cardiac events could be used independently or in conjunction with a ST segment or T wave shift detectors to sense a cardiac event.

It is also envisioned that all of the processing techniques described herein for an implantable cardiosaver are applicable to a guardian system configuration using skin surface electrodes and a non-implanted cardiosaver 5 the term electrogram would be replaced by the term electrocardiogram. Thus the cardiosaver device described in FIGS. 5 through 12 would also function as a monitoring device that is completely external to the patient.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A system for detecting a cardiac event in a human patient the system including:
   (a) at least two sensors configured for obtaining an electrical signal from the patient's heart,
   (b) analog-to-digital converter circuitry for digitizing the signal to produce data segments having a time duration between 3 and 30 seconds;
   (c) a implantable processor configured to:
      (i) process the data segments to identify cardiac activity related to each heart beat, each beat being a sub-segment of the data segment having a measurable R-R interval from the preceding beat;
      (ii) compute the R-R intervals of beats in each of the data segments, thereby generating a plurality of R-R intervals;
      (iii) based upon the plurality of R-R intervals, categorize the rate of each of the data segments; in each categorized data segment, determine between the segment having ST deviations above a predetermined threshold and data segments having ST deviations below a predetermined threshold;
      (iv) perform ischemia detection on at least one of the data segments with the ST deviation above said predetermined threshold;
      (v) based at least on the categorized rate and on the ischemia detection performed on one of the data segments with the ST deviation above said predetermined threshold, determine between ischemia being present and ischemia not being present;
      (vi) operative upon determining that ischemia is present for a predetermined number of beats within the data segment, generate a first alarm event and transmit said first alarm event to an external receiver for notification of said first alarm event;
      (vii) operative upon determining that ischemia is not present, generating a second different alarm event upon determining if a number of further data segments are segments with the ST deviation above said predetermined threshold for a predetermined number of beats within at least one of the further data segments.

2. The system of claim 1 wherein data segments with the ST deviation include low heart rate segments.

3. The system of claim 2 wherein data segments with the ST deviation include high heart rate segments.

4. The system of claim 3 wherein further data segments that are elevated after a detection of low heart rate data segments are checked for ischemia, but high heart rate data segments are not checked for ischemia.

5. The system of claim 1 wherein data segments with the ST deviation include unsteady heart rate segments.

6. The system of claim 1 wherein the sensors comprise electrodes.

7. The system of claim 6 wherein at least one of the electrodes is adapted for implantation within a heart.

* * * * *